United States Patent
Schmitz et al.

(10) Patent No.: US 7,239,385 B2
(45) Date of Patent: Jul. 3, 2007

(54) METHOD AND APPARATUS FOR MONITORING OUTPUT SIGNAL INSTABILITY IN A LIGHT SOURCE

(75) Inventors: Roger W. Schmitz, Hutchinson, MN (US); Bryan J. Scheele, Hutchinson, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 310 days.

(21) Appl. No.: 10/999,260

(22) Filed: Nov. 30, 2004

(65) Prior Publication Data

US 2006/0114457 A1    Jun. 1, 2006

(51) Int. Cl.
*G01J 3/42* (2006.01)
(52) U.S. Cl. ...................... 356/319; 356/300
(58) Field of Classification Search ................ 356/319
See application file for complete search history.

(56) References Cited

U.S. PATENT DOCUMENTS

| | | | |
|---|---|---|---|
| 3,830,972 | A | 8/1974 | McHugh et al. |
| 4,257,709 | A | 3/1981 | Mostyn, Jr. |
| 4,323,309 | A | 4/1982 | Akitomo et al. |
| 4,566,797 | A | 1/1986 | Kaffka et al. |
| 4,625,315 | A | 11/1986 | Lemberger et al. |
| 4,661,693 | A | 4/1987 | Masanobu |
| 4,684,245 | A | 8/1987 | Goldring |
| 4,800,266 | A | 1/1989 | Poorman |
| 4,913,150 | A | 4/1990 | Cheung et al. |

(Continued)

FOREIGN PATENT DOCUMENTS

EP    0182647 A2    11/1985

(Continued)

OTHER PUBLICATIONS

Aleksanyan et al., "Stabilization and Calibration of Hodoscopic Cerenkov Spectrometer", *Instruments and Experimental Techniques*, Jul.-Aug. 1987, pp. 793-797, vol. 30, No. 4 Part 1, Plenum Publishing Corporation, Consultants Bureau, New York (translated from Russian).

(Continued)

*Primary Examiner*—F. L. Evans
(74) *Attorney, Agent, or Firm*—Faegre & Benson LLP

(57) ABSTRACT

A spectrophotometric instrument is comprised of a processor, a probe having a tissue engaging surface with an aperture therethrough and a light source producing measurement light signals and optically coupled to the probe via a first optical path. A partially reflective first reflecting member is located in the probe and has a generally elliptical profile positioned to reflect a first portion of the measurement light signals to the tissue aperture and to transmit a second portion of the measurement light signals through the first reflecting member. A second reflecting member is located in the probe and has a generally elliptical profile positioned to reflect the measurement light signals transmitted through the first reflecting member. A second optical path has a distal end positioned to receive the measurement light signals reflected off of the second reflecting member and a proximal end coupled to the processor. A third optical path has a distal end positioned in the probe to receive light signals transmitted through the tissue sample and a proximal end coupled to the processor.

39 Claims, 13 Drawing Sheets

U.S. PATENT DOCUMENTS

| | | | |
|---|---|---|---|
| 5,005,699 A | 4/1991 | Kawashima et al. | |
| 5,039,224 A | 8/1991 | O'Rourke et al. | |
| 5,157,250 A | 10/1992 | Oikari et al. | |
| 5,259,382 A | 11/1993 | Kronberg | |
| 5,377,000 A | 12/1994 | Berends | |
| 5,477,853 A | 12/1995 | Farkas et al. | |
| 5,522,389 A | 6/1996 | Fischer et al. | |
| 5,783,909 A | 7/1998 | Hochstein | |
| 5,807,261 A | 9/1998 | Benaron et al. | |
| 5,879,294 A | 3/1999 | Anderson et al. | |
| 5,894,539 A | 4/1999 | Epstein | |
| 6,006,119 A | 12/1999 | Soller et al. | |
| 6,052,177 A * | 4/2000 | Millar et al. | 356/73 |
| 6,215,936 B1 | 4/2001 | Yoshikawa et al. | |
| 6,304,767 B1 | 10/2001 | Soller et al. | |
| 6,347,874 B1 | 2/2002 | Boyd et al. | |
| 6,366,409 B1 | 4/2002 | Umemoto et al. | |
| 6,377,840 B1 | 4/2002 | Gritsenko et al. | |
| 6,473,165 B1 * | 10/2002 | Coombs et al. | 356/71 |
| 6,481,899 B1 | 11/2002 | Quast et al. | |
| 6,487,343 B1 | 11/2002 | Lewandowski et al. | |
| 6,554,440 B2 | 4/2003 | Umemoto | |
| 6,556,851 B1 | 4/2003 | Ott et al. | |
| 6,667,803 B1 | 12/2003 | Flessland et al. | |
| 2004/0236198 A1 * | 11/2004 | Gritsenko | 600/323 |

FOREIGN PATENT DOCUMENTS

| | | |
|---|---|---|
| EP | 0262878 A1 | 9/1987 |
| EP | 0781527 A1 | 11/1996 |
| GB | 2014751 A | 1/1979 |
| GB | 2269012 A | 7/1993 |

OTHER PUBLICATIONS

Mangoyanov et al., "Stabilization System for Multidetector Scintillation Spectrometer", *Instruments and Experimental Techniques*, Mar.-Apr. 1969, pp. 76-81, No. 2, Joint Institute for Nuclear Research, Dubna (translated from Russian).

Reiter et al., "A Long Term Stable Reference Light Source Using Leds for Stabilization of Scintillation Spectrometers", *Nuclear Instruments and Methods*, Feb. 1980, pp. 275-282, No. 173, North-Holland Publishing Company.

Hutchinson Technology, Inc., BioMeasurement Division, "InSpectra™ Tissue Spectrometer Model 325 User and Service Manual", U.S. Version, Mar. 5, 2002.

* cited by examiner

METHOD AND APPARATUS FOR MONITORING OUTPUT SIGNAL INSTABILITY IN A LIGHT SOURCE

TECHNICAL FIELD

The present invention relates to the field of light based measurements and more particularly to methods and structures for monitoring and compensating for the output signal instability of a light source.

BACKGROUND OF THE INVENTION

Spectrometers have gained popularity as a tool for measuring attributes of tissue. By way of illustration only, the operation of an instrument of this type is described briefly with reference to prior art FIG. 1. As shown, the instrument 10 included an optical probe 12 which was releasably connected to an electronics package 14 via optical fibers 16. The electronics package 14 included a connector 18, a detector 20, a processor/controller 22, and a display 24. In operation, the probe 12 was positioned on the tissue to be measured or analyzed. The probe 12 was interfaced to the instrument electronics through the optical fibers 16 and a probe connector 26. Referring now to prior art FIG. 2, the probe connector 26 included light emitting diodes (LEDs) or other light sources 30, 32, 34, 36, and 38 for generating light at a number of different wavelengths (e.g., 800, 760, 720, 680, and 530 nm, respectively). The light used to measure the characteristics of the tissue was coupled to the probe 12 by send optical fibers 40, 42, 44, and 46. After being transmitted from the tissue-engaging surface of the probe 12 into the tissue being measured, the light traveled through the tissue before being collected at the end of the receive optical fiber 48. This collected light (measurement light signal) was then transmitted to the instrument 14 through the probe connector 26 and electronics package connector 18. A reference light signal corresponding to each of the measurement light signals (i.e., the reference light signals were not transmitted through the tissue) was also transmitted to the electronics package connector 18. The optical probe 12 is described in greater detail in Provisional U.S. Patent Application Ser. No. 60/137,383 entitled "Disposable Tissue Probe Tip" and U.S. Pat. No. 6,487,343 entitled "Fiber Optic Light Mixer."

The collected measurement light signals and reference light signals received by the electronics package 14 were transmitted to the detector 20 which produced electrical signals representative of these light signals at each wavelength of interest. The processor/controller 22 then processed these signals to generate data representative of the measured tissue parameter (e.g., saturated oxygen level ($StO_2$)). The measurement reading could have been visually displayed on the display 24. Algorithms used to compute the tissue parameter data are generally known and described in U.S. Pat. No. 5,879,294 entitled "Tissue Chromophore Measurement System."

Calibration procedures were typically performed to enhance the accuracy of the measurements subsequently made by the instrument 14. Methods and devices for calibrating spectrophotometric-type instruments are generally known and disclosed in the above-referenced U.S. patent entitled "Tissue Chromophore Measurement System." The calibration could have, for example, been performed by placing the probe 12 on a calibration device 50 such as that shown in FIG. 1. The calibration device 50 included a housing which was filled with light scattering material. The light scattering material was generally spectrally flat (i.e., reflects all light to the same degree) to provide a reference spectrum. White polyethylene foam such as Plastazote LD45 available from Zotefoams, Inc. could have been used for this purpose.

One configuration of a spectrophotometric instrument of the type described above included, for each wavelength of interest, a photomultiplier tube (PMT) for detecting the measurement light signal, and a photodiode for detecting the calibration recognition signal (or ambient light). Thermal electric coolers could have been included in the electronics package to help maintain temperature control of the optical bench to which the PMTs and photodiodes were mounted, and thereby reduce output signal drift.

The probe connector 26 used in connection with this device is illustrated in prior art FIG. 2, which shows an embodiment having a reference signal generated within the connector 26. As shown, the probe connector 26 included 4 LED's 30, 32, 34, and 36 for generating the measurement light signals at 800, 760, 720 and 680 nm. Light signals from each of these LEDs were coupled to the probe 12 by a separate measurement signal send fiber 40, 42, 44, 46. After being transmitted through the tissue being analyzed and collected at the probe, the measurement light signal was coupled back to the probe connector 26 by a measurement signal receive fiber 48. The end of the measurement signal receive fiber 48 terminated in the probe connector 26 at a sample ferrule 52 which was adapted to mate with a socket in the connector 18 of the electronics package 14. The optical probe 12 is described in greater detail in the above-referenced Provisional U.S. Patent Application entitled "Disposable Tissue Probe Tip" and U.S. Patent entitled "Fiber Optic Light Mixer."

A reference light signal was also provided by the probe connector 26. The reference light signal included a portion of the light from each of the LEDs, and had not been transmitted from the probe 12 before being collected. In the embodiment shown in FIG. 2, the reference light signal was collected by reference light signal send optical fibers 54, 56, 58 and 60, which extended respectively from each measurement light signal source LED 30, 32, 34, 36 to a light mixer/attenuator 62 formed by scattering material attached to a reference fiber fixturing ferrule 64. The reference signal send fibers 54, 56, 58, 60 were collected in the fixturing ferrule 64 at the scattering material along with a reference signal receive fiber 66. The reference light received from each LED was mixed at the mixer 62 and transmitted through the reference signal receive fiber 66. The end of the reference signal receive fiber 66 terminated in the probe connector 26 at a reference ferrule 68 which was adapted to mate with a socket in the connector 18 of the electronics package 14.

Since it was significantly attenuated when it was transmitted through the tissue, the intensity of the measurement light signal at the connector 26 was much less than the intensity of the non-attenuated reference light signal (e.g., about 1 million times less). In order to match the reference and measurement signal magnitudes to enable detection with a similar photo multiplier tube gain, the reference signal was attenuated at the mixer 62. The reference signal attenuation was obtained by reflectance mode positioning the reference signal send fibers 54, 56, 58, 60 equidistant from the centrally located reference signal receive fiber 66. The concentration of scattering material (such as titanium dioxide from Aldrich, Milwaukee, Wis.) within an optically clear epoxy substrate (such as EpoTech 301 from Epoxy Technology, Billerica, Mass.) could have been adjusted to provide the appropriate level of attenuation within the mixer 62. The probe connector 26 also preferably had a 14 pin electrical connector 72 and an optical fiber fixturing ferrule 74 for each of the LED's 30, 32, 34, 36, and 38, each of which were mounted in a PC board 76, along with connector 72. LED 38 was a calibration recognition signal LED connected to a calibration recognition send fiber 78. It is to be understood that the arrows on fibers 40, 42, 44, 46 were to indicate "to probe tip" while the arrows on fiber 48 were to indicate "from probe tip."

A connector latch mechanism (not shown) latched the sample ferrule 52 and reference ferrule 68 of the probe connector 26 to the corresponding sockets (not shown) of the connector 18 in the electronics package 14. The latch connector mechanism is described in greater detail in U.S. Pat. No. 6,481,899 entitled "Optical Connector Latch Mechanism for Spectrophotometric Instrument."

The reference light signal and measurement light signal (also referred to as a sample light signal) received at the connector 18 at spatially separated paths were collimated by lenses or other optics and directed to a shutter and path-shifting optics 80 (prior art FIG. 3). The shutter and path-shifting optics 80 selectively and alternately directed or folded the signals into a common path to the detector 20 (optical bench). One embodiment of the shutter and path-shifting optics 80 is illustrated in FIG. 3. As shown, a 30° stepper motor 87 drove opaque vane 84 and was controlled by the processor/controller 22, as indicated by arrow 86. The stepper motor 87 positioned the vane 84 to selectively block one of the reference light signal and measurement light signal, and to transmit the other of signals to the path-shifting optics 80. Arrow 88 indicates a collimated LED reference light path, while arrow 90 indicates a collimated measurement/sample light path (from the probe 12).

In the embodiment shown, the path shifting optics 80 included a 45° combining (beam splitting) reflecting member 92 in the measurement light path 94. This combining reflecting member 92 allowed a significant portion (e.g., 98–99%) of the measurement light signal to pass through the reflecting member 92 to the detector 20 (see FIG. 1) as indicated by arrow 96, with the remaining amount (e.g., 1–2%) being reflected away from the detector 20 (i.e., trapped, as indicated by arrow 98). A 45° reflecting member 100 in the reference light path 102 reflected the reference light signal onto the side of the combining reflecting member 92 opposite the side to which the measurement light signal was initially directed. A significant portion of the reference light signal would then pass through the combining reflecting member 92, while a smaller amount (e.g., 1–2%) would be reflected to the detector 20 (see FIG. 1) along the same optical path 96 as the measurement light signal. The measurement light signal and reference light signal were thereby directed or folded onto the same path 96 and directed to a common detector. In response to control signals from the processor/controller 22 (see FIG. 1), the stepper motor 87 would position the opaque vane 84 to block one of the reference light signal or the measurement light signal. The other of the reference light signal and the measurement light signal would then be transmitted to the detector 20. This optics configuration also reduced the intensity of the reference light signal so it would not saturate the PMTs of the detector 20.

Prior art FIG. 4 is an illustration of a detector 20 for use in the instrument 10 or electronics package 14 shown in prior art FIG. 1 and described above. An approximate 5 mm diameter collimated light beam indicated by arrow 104 (either from the reference or sample (measurement) light signal) was transmitted to the front surface of an 800 nm dichroic reflecting member 106 which was positioned 30° from an optical axis 108. Approximately 90% of the light having a wavelength greater than 780 nm was reflected to a first photomultiplier tube (PMT) sensor 110 which had an 800 nm bandpass filter (+/−10 nm at full-width, half-maximum (FWHM)) positioned in front of the PMT sensor 110. Approximately 80% of the light having a wavelength shorter than 780 nm was transmitted through the 800 nm dichroic reflecting member 106 to the front surface of a 760 nm dichroic reflecting member 112 which was positioned 25° from the optical axis 108. Approximately 90% of the light having a wavelength greater than 740 nm was reflected to a second PMT sensor 114 which had a 760 nm bandpass filter (+/−10 nm FWHM) positioned in front of the PMT sensor 114. Approximately 80% of the light having a wavelength shorter than 740 nm was transmitted through the 760 nm dichroic reflecting member 112 to the front surface of a 720 nm dichroic reflecting member 116 which was positioned 30° from the optical axis 108. Approximately 90% of the light having a wavelength greater than 700 nm was reflected to the third PMT sensor 118 which had a 720 nm bandpass filter (+/−10 nm FWHM) positioned in front of the PMT sensor 118. Approximately 80% of the light having a wavelength shorter than 700 nm was transmitted through the 720 nm dichroic reflecting member 116 to the front surface of a 680 nm dichroic reflecting member 120 which was positioned 30° from the optical axis 108. Approximately 90% of the light having a wavelength greater than 660 nm is reflected to the fourth PMT sensor 122 which had a 680 nm bandpass filter (+/−10 nm FWHM) positioned in front of the PMT sensor 122. Approximately 80% of the light having a wavelength shorter than 660 nm was transmitted through the 680 nm dichroic reflecting member 120 to a detector block consisting of a 600 nm short pass filter (transmitted light from approximately 400 nm to 600 nm) positioned in front of a photo diode detector. This detector was used to measure the presence of ambient light and/or the calibration material recognition signal (530 nm LED emitter). The calibration material recognition signal and the manner by which it was used is described in U.S. Pat. No. 6,667,803 entitled "Calibration Mode Recognition And Calibration Algorithm For Spectrophotometric Instrument."

During calibration procedures performed by the instrument, and for each of the PMTs used in connection with the calculation of the measurement (4 PMTs in the described embodiment), a baseline reading was established for both the measurement signal received from the probe (i.e., a baseline sample) and the reference signal (i.e., a baseline reference). These calibration measurement and reference baseline signals (for each PMT) were obtained through the use of the shutter and path-shifting optics 80 described above, and were stored in memory (not separately shown) and subsequently used in the measurement calculation algorithm.

Prior art FIG. 5 illustrates an optical probe 130 which was used in connection with the instrument shown in the above referenced U.S. Patent entitled "Tissue Chromophore Measurement System" and which included a light mixer 132. The probe 130 included an insert 134 for holding a number of optical fibers 136, 138, and 140, a housing 142 into which the insert 134 was mounted and a disposable elastomeric tip (not shown) which was releasably mounted to the housing 142. The optical fiber 136 terminated at a mixing fiber 144 and was coupled between the housing 142 and instrument within a cable housing 146. The illustrated embodiment of the probe 130 had four send fibers 136 through which light of different wavelengths from the instrument (provided by narrow bandwidth LEDs) was transmitted to the probe 130. The ends of the send fibers 136 were sealed in a ferrule 148. The light mixer 132 was a section of optical fiber 144 located between the fiber ferrule 148 and a tissue-facing surface 150 of the probe 130. The light mixer 132 accepted, on its input side, light from the individual send fibers 136. The light mixer 132 enhanced the homogeneity of the light emitted on its output side and transmitted to the tissue. Each wavelength of light was scattered over the whole cross-sectional area of the fiber 144 of the mixer 132, enabling each wavelength of light to travel through a similar volume of tissue.

As shown, the send fibers 136 were bent or formed to direct the ends at a 90° angle with respect to the tissue-facing surface 150. The different wavelengths of light emitted from the ends of the send fibers 136 were mixed within the fiber 144 of mixer 132 and thereby scattered throughout the surface area of the fiber 144 at the tissue-facing surface 150. As shown, a receive fiber 138 and a calibration recognition fiber 140 also had ends which terminated at the tissue-facing surface 150 of the probe 130. The receive fiber 138 collected light that traveled through the tissue being analyzed and transmitted the collected light to the instrument for processing. Light emitted from the calibration recognition fiber 140 was used by the instrument to control a calibration procedure.

Typical prior art instruments directed measurement light signals onto the tissue sample by bending the optical fibers in the probe to direct the light onto the tissue (see FIG. 5). The typical minimum recommended bend radius for an optical fiber is twenty times the fiber diameter, although this number may vary widely depending upon the type of optical fiber. Bending or shaping an optical fiber at less than the recommended minimum bend radii results in signal impairment or light signal loss, temperature sensitivity, and broken fibers. However, desirable spatial limitations in a probe are generally not suited to accommodate the minimum recommended bend radius of optical fibers. Generally, smaller sized probes are desirable for engaging smaller tissue sample areas and/or smaller test subjects, and are considered to be more comfortable and less intrusive for the test subject. As a result, prior art instruments were either large enough to accommodate the minimum recommended bend radius of the optical fibers, or produced lower quality light signals through over-bending of the optical fibers.

While the prior art structure for putting light at the surface of the tissue under study worked, high signal losses were encountered in the path between the LEDs and the tissue. Further, significant manufacturing effort and parts costs were incurred to make all of the optical paths required. Also, calibration procedures had to be repeated periodically to compensate for drift in the light source wavelength.

SUMMARY OF THE INVENTION

The present invention, according to one embodiment, is a probe for a spectrophotometric instrument. The probe includes a probe housing, and first, second and third optical paths. The probe housing has a tissue engaging surface with first and second apertures extending therethrough. The first optical path has a proximal end optically coupleable to a light source and extends to a distal end optically coupled to the first aperture for delivering a beam of measurement light signals to a tissue sample. The second optical path has a distal end optically coupled to the first optical path adjacent the first aperture for sampling a reference light signal portion of the measurement light signals of the first optical path. The second optical path extends to a proximal end coupleable to a processor. The third optical path has a distal end optically coupled to the second aperture and extends to a proximal end coupleable to the processor.

The present invention, according to another embodiment, is a feedback system for monitoring output signal instability of a spectrophotometric instrument. The system includes a probe, a first optical path and a second optical path. The probe has a tissue engaging surface with a first aperture extending therethrough. The first optical path has a proximal end optically coupleable to a light source and extends to a distal end optically coupled to the first aperture for delivering a beam of measurement light signals to a tissue sample. The second optical path has a distal end optically coupled to the first optical path adjacent the first aperture for sampling a portion of the measurement light signals of the first optical path and extends to a proximal end coupleable to a processor.

The present invention, according to yet another embodiment, is a probe for use with a spectrophotometric instrument. The probe includes a probe housing, a first optical path, a feedback means and a third optical path. The probe housing has a tissue engaging surface with first and second apertures extending therethrough. The first optical path has a proximal end optically coupleable to a light source and extends to a distal end optically coupled to the first aperture for delivering a beam of measurement light signals to a tissue sample. The feedback means is for removing a portion of the measurement light signals from the first optical path adjacent the first aperture representative of the measurement light signals striking the tissue sample. The third optical path has a distal end optically coupled to the second aperture and extends to a proximal end coupleable to a processor.

The present invention, according to still another embodiment, is a method for monitoring output signal instability in a spectrophotometric instrument. A probe is provided having a tissue engaging surface for delivering measurement light signals to a tissue sample and for receiving light emitted from the tissue sample. A light source assembly is provided for generating the measurement light signals. The light source assembly includes a light source and at least one send optical fiber optically coupling the light source to the probe. The send optical fiber has a proximal end optically coupled to the light source and a distal end protruding into the probe parallel to the tissue engaging surface. Measurement light signals are delivered from the light source assembly to the probe through the send optical fiber. The measurement light signals are reflected from the distal end of the send optical fiber onto the tissue sample. A reference sample of the measurement light signals representative of the measurement light signals reflected onto the tissue sample is removed.

DETAILED DESCRIPTION OF THE INVENTION

Figure 6:
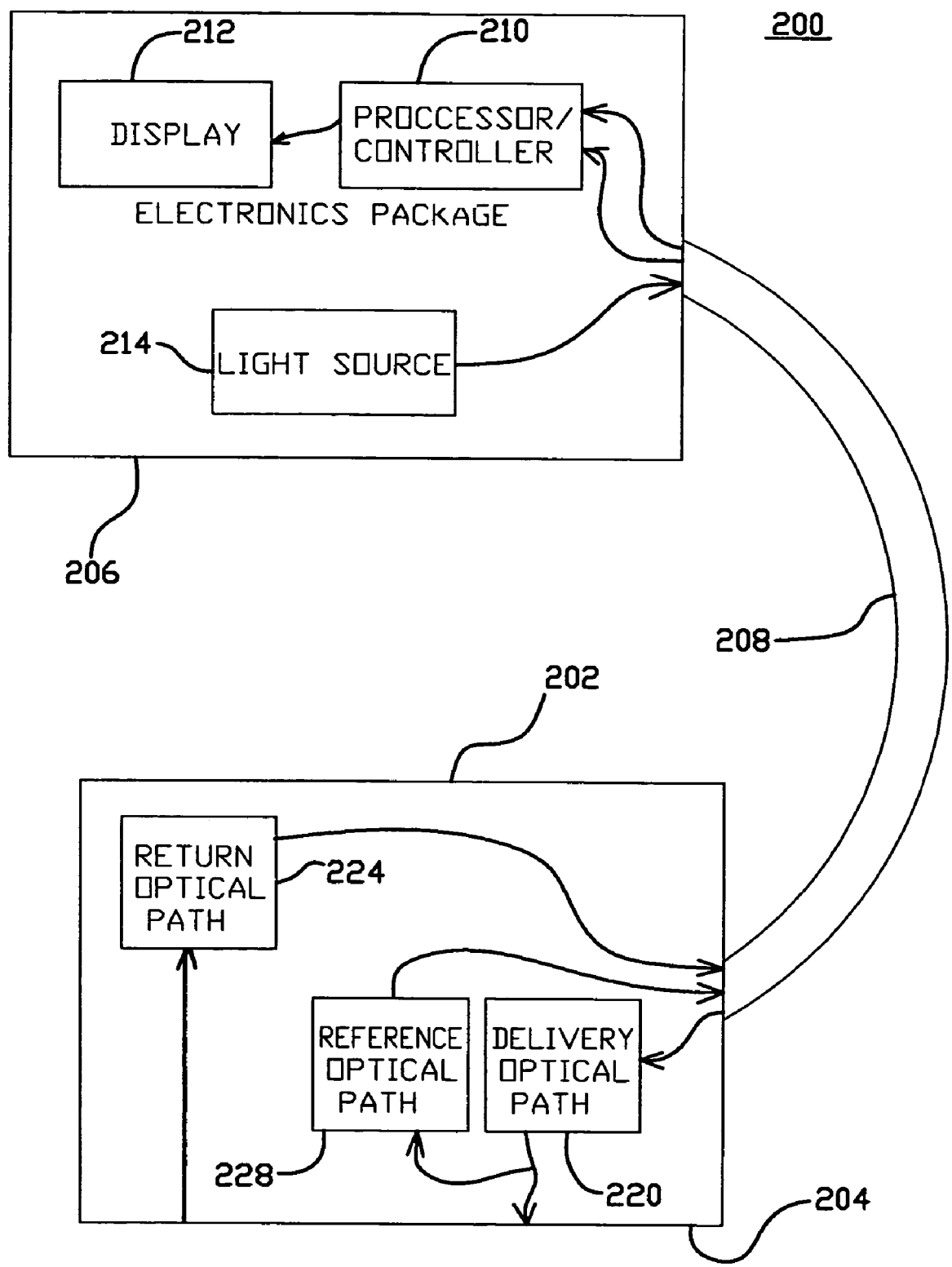
FIG. 6 is a block diagram of a spectrophotometric instrument according to one embodiment of the present invention.

FIG. 6 is a block diagram of a spectrophotometric instrument 200 for determining the relative concentration of a first tissue chromophore with respect to a second tissue chromophore in a tissue sample by measuring the absorption of light transmitted through the tissue according to one embodiment of the present invention. An optical probe 202 is releasably operably coupled to an electronics package 206 via a connector 208. The electronics package 206 includes a processor/controller 210, a display 212 and a light source 214. Light source 214 may include LEDs or other light sources for generating light at a number of different wavelengths (e.g., 800, 760, 720, and 680 nm). Measurement light signals from the light source 214 travel along the connector 208 to a delivery optical path 220 housed in the probe 202. The measurement light signals travel along the delivery optical path 220 from the connector 208 to a tissue engaging surface 204 of the probe 202 and into the tissue sample. A reference signal portion of the measurement light signals are diverted after they have traveled through the delivery optical path 220 into a reference optical path 228 (i.e., the reference light signal is not transmitted through the tissue sample). Light signals, including measurement light signals that have traveled through the tissue sample, are collected at the tissue engaging surface 204 and travel along a return optical path 224 through the probe 202. Light signals from the reference optical path 228 and the return optical path 224 travel along the connector 208 to the electronics package 206. The collected light signals and reference light signals received by the electronics package 206 are employed by the processor/controller 210 to generate data representative of the measured tissue parameter (e.g., saturated oxygen level ($StO_2$)). The data is then displayed on the display 212. The reference light signals are also employed by the processor/controller 210 to monitor output signal instability of the light source 214.

Figure 7A:
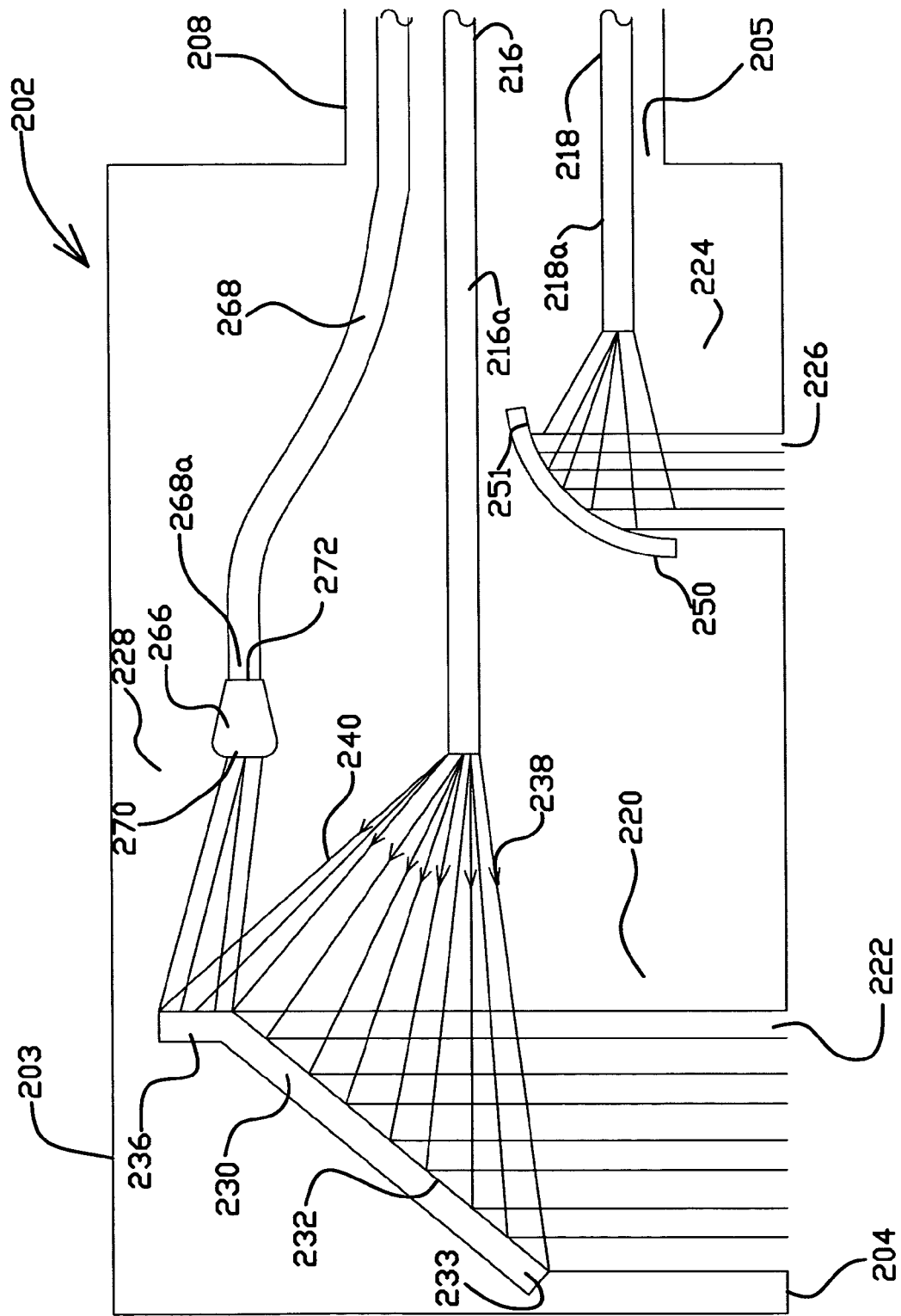
FIG. 7A is a side sectional view of the probe of FIG. 6 according to one embodiment of the present invention.

FIG. 7A illustrates the probe 202 and a portion of the connector 208 of FIG. 6 in accordance with one embodiment of the present invention. The probe 202 includes a probe housing 203 including the tissue engaging surface 204. The tissue engaging surface 204 is provided with a first delivery aperture 222 and a second return aperture 226 extending therethrough. The delivery aperture 222 and return aperture 226 permit delivery of measurement light signals to the tissue sample and collection of light signals from the tissue sample, respectively.

The probe housing 203 is provided with a connector aperture 205 extending therethrough for receiving a distal end of the connector 208. In one embodiment, the connector 208 is coupled to the housing 203 via an adhesive, clips, or other suitable means. According to another embodiment, the connector 208 is constructed integrally with the probe housing 203. According to yet another embodiment, the connector 208 is detachably coupled to the probe housing 203.

The connector 208 includes at least one send optical fiber 216 coupled to the light source 214 for transmitting measurement light signals from the light source 214 to the probe housing 203. A mechanism for coupling an optical fiber such as optical fiber 216 to a light source such as light source 214 is described in commonly assigned pending U.S. patent application entitled "Light Source Structure" which is incorporated herein. According to one embodiment, measurement light signals of varying wavelengths from a plurality of light sources 214 are combined together in the electronics package 206 and travel along a single send optical fiber 216 to the probe 202. According to other embodiments, individual or a plurality of send optical fiber 216 are coupled to each light source 214. A distal end 216a of the optical fiber 216 extends into the probe housing 203 through the connector aperture 205. The send optical fiber 216 extends into the probe housing 203 at an angle approximately parallel to the plane of the tissue engaging surface 204.

The delivery optical path 220 of FIG. 7A includes a reflecting member 230 having a reflecting surface 232 positioned adjacent the distal end 216a of the send optical fiber 216. The reflecting member 230 is positioned relative to the distal end 216a of the send optical fiber 216 and the plane of the tissue engaging surface 204 so that measurement light signals exiting the distal end 216a of the send optical fiber 216 strike the reflective surface 232 and are reflected through the delivery aperture 222 in the tissue engaging surface 204 and onto the tissue sample. According to one embodiment, a first portion 233 of the reflecting member 230 is positioned at about a 45° angle with respect to distal end 216a of the send optical fiber 216 and the tissue engaging surface 204.

In operation, a generally circular beam of measurement light signals exits the distal ends 216a of the send optical fibers 216 and a first region of the beam as shown by arrows 238 is reflected off of the reflective surface 232 at the first portion 233 of the reflecting member 230. The beam of reflected measurement light signals is directed through the delivery aperture 222 onto the tissue sample. According to one embodiment, the reflected measurement light signals are directed onto the tissue sample at angles ranging from about 70° to about 110° relative to the surface of the tissue sample. According to another embodiment, the measurement light signals are directed onto the tissue sample at a distribution about a perpendicular angle relative to the surface of the tissue sample.

It is generally preferable that measurement light signals be directed onto the tissue sample approximately perpendicular to the surface of the tissue sample. Such a configuration increases the likelihood that all measurement light signals travel the same distance through the tissue sample. A probe 202 according to the present invention directs the measurement light signals onto the tissue sample at a perpendicular angle relative to the surface of the tissue sample by reflecting the measurement light signal beam rather than by bending the send optical fibers 216. The probe housing 203 need not accommodate the minimum bend radius of the optical fibers 216, typically at least twenty times the fiber diameter. Rather, the probe housing 203 need only accommodate the diameter of the send optical fibers 216 protruding into the probe housing 203. A probe housing 203 according to the present embodiment is smaller than prior art probes, or alternately provides increased space for other components within the probe housing 203. Measurement light signal quality is also improved by reducing excessive bending of the send optical fibers 216. A probe 202 according to the present invention is also less likely to require repair, as the send optical fibers 216 are subjected to less bending stress, and are less likely to break or require replacement.

The return optical path 224 includes a reflecting member 250 positioned adjacent the return aperture 226 and a return optical fiber 218 for transmitting collected light signals from the probe 202 back to the electronics package 206. Light, including measurement light signals transmitted through the tissue sample, is reflected on a reflective surface 251 of the reflecting member 250 and directed toward a distal end 218a of the return fiber 218. The reflective surface 251 has a curved profile shaped to narrow or focus the reflected light signals onto the distal end 218a of the return fiber 218. The collected light is transmitted through the return fiber 218 within the connector 208 to the electronics package 206. In this manner, similar to the structure of the delivery optical path 220, the return fiber 218 need not be bent to collect light signals transmitted through the tissue sample. A probe 202 having a reduced size and profile is therefore provided. According to other embodiments (not shown), reflecting member 250 is generally planar, as is described with respect to the first reflecting member 230.

Reflecting member 230 is further provided with a second portion 236 formed at an angle with respect to the first portion 233. The second portion 236 is shaped or positioned to reflect measurement light signals to the feedback optical path 228. As the beam of measurement light signals from the send optical fibers 216 is directed to reflecting member 230, a second region of the beam of measurement light signals as represented by arrows 240 is reflected off of the second portion 236 of the reflecting member 230 so that the measurement light signals of the second region 240 diverge from those of the first region 238 and are directed to the feedback optical path 228. The measurement light signals of the second region 240 correspond to approximately 1–20% of the measurement light signals overall.

The feedback optical path 228 includes a diffusing member 266 coupled to a distal end 268a of a feedback optical fiber 268. In the present embodiment, diffusing member 266 is comprised of a bulk media and has a first surface 270 positioned to receive feedback light signals and a second surface 272 optically coupled to the distal end 268a of the feedback optical fiber 268. First surface 270 has a generally larger surface area than second surface 272 such that the diffuser 266 tapers between the first surface 270 and the second surface 272. Diffusing member 266 is positioned to receive the diverted or feedback portion of the measurement light signals at the first surface 270 and transmit them to the feedback optical fiber 268 at the second surface 272. In this manner, the diameter of the beam of feedback light signals is reduced between the first surface 270 and the second surface 272 of the diffuser 266 so as to match the diameter of the feedback optical fiber 268. This feature compensates for differences in size between the beam of feedback light signals and the diameter of the distal end 268a of the feedback optical fiber 268. According to one embodiment, the first surface 270 is curved outwardly to have a generally convex shape. The first surface 270 is curved so that the linear distance traveled by the reference light signals from the first surface 270 to the distal end 268a of the reference optical fiber 268 is generally equal regardless of the location the reference light signals strike the first surface 270.

Diffusing member 266 renders the coupling efficiency, or the amount of reference light signals transmitted to the optical fiber 268 relative to the amount of reference light signals striking the first surface 270 independent of the angle at which the reflected reference light signals strike the diffusing member 266 and the spatial distribution of the reference light signals on the first surface 270. In other words, regardless of where or at what angle the reference light signals strike the first surface 270, approximately the same percentage of the light signals are transmitted to the feedback optical fiber 268.

Figure 1:
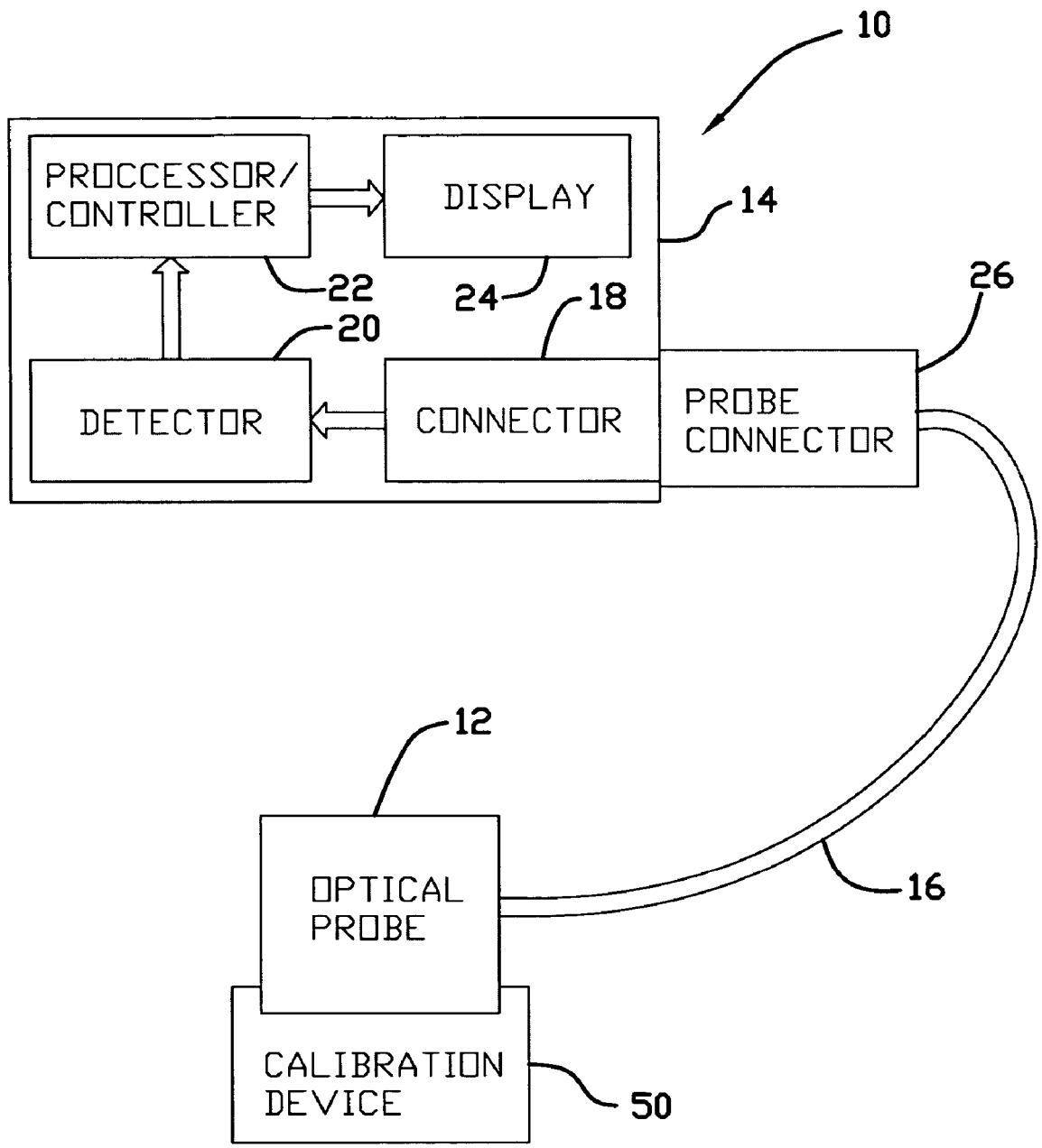
FIG. 1 is a block diagram of a prior art spectrophotometric instrument.
Figure 2:
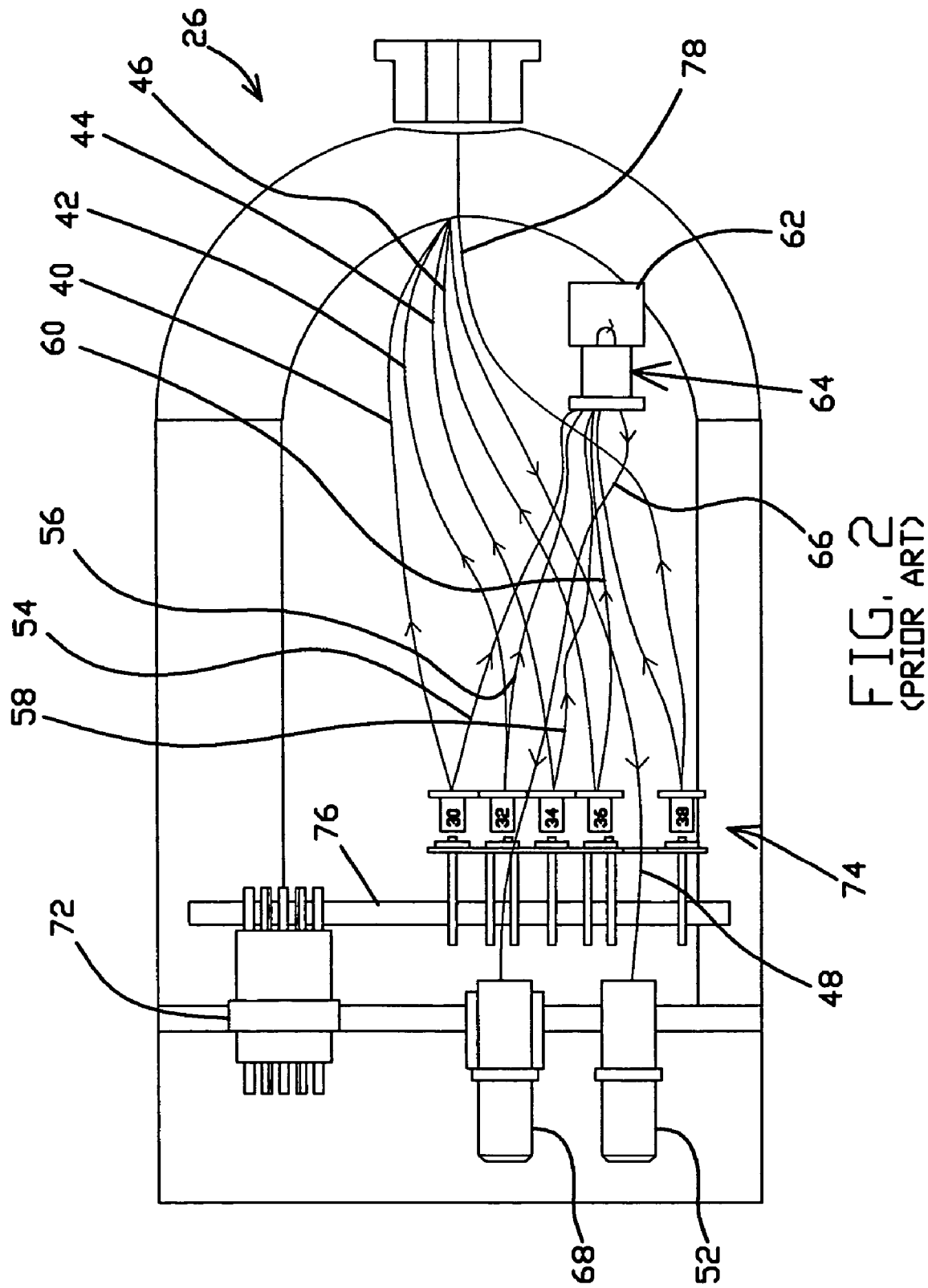
FIG. 2 is a side sectional view of the prior art probe connector of FIG. 1.
Figure 3:
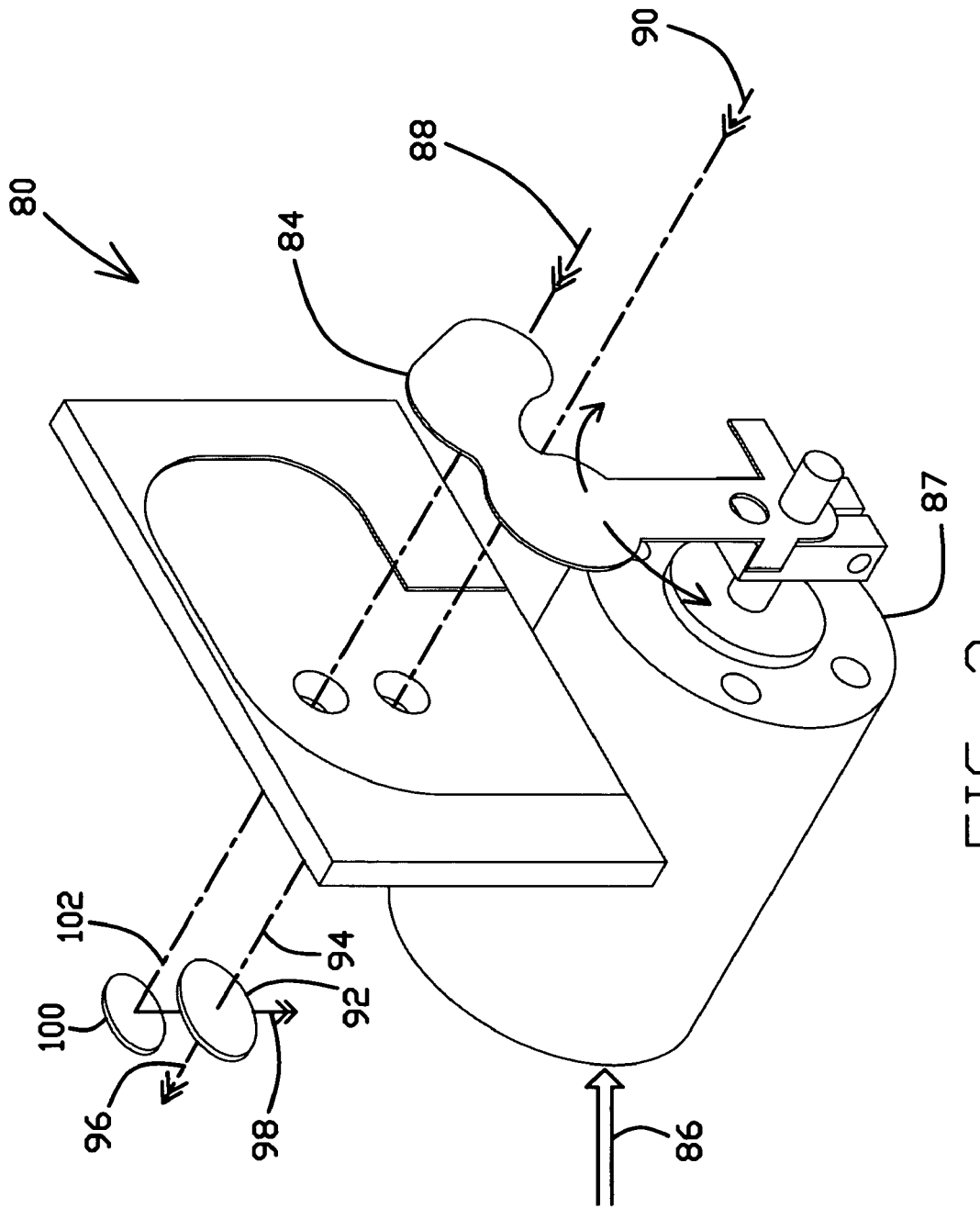
FIG. 3 is a perspective view of a portion of the prior art connector of FIG. 1.
Figure 4:
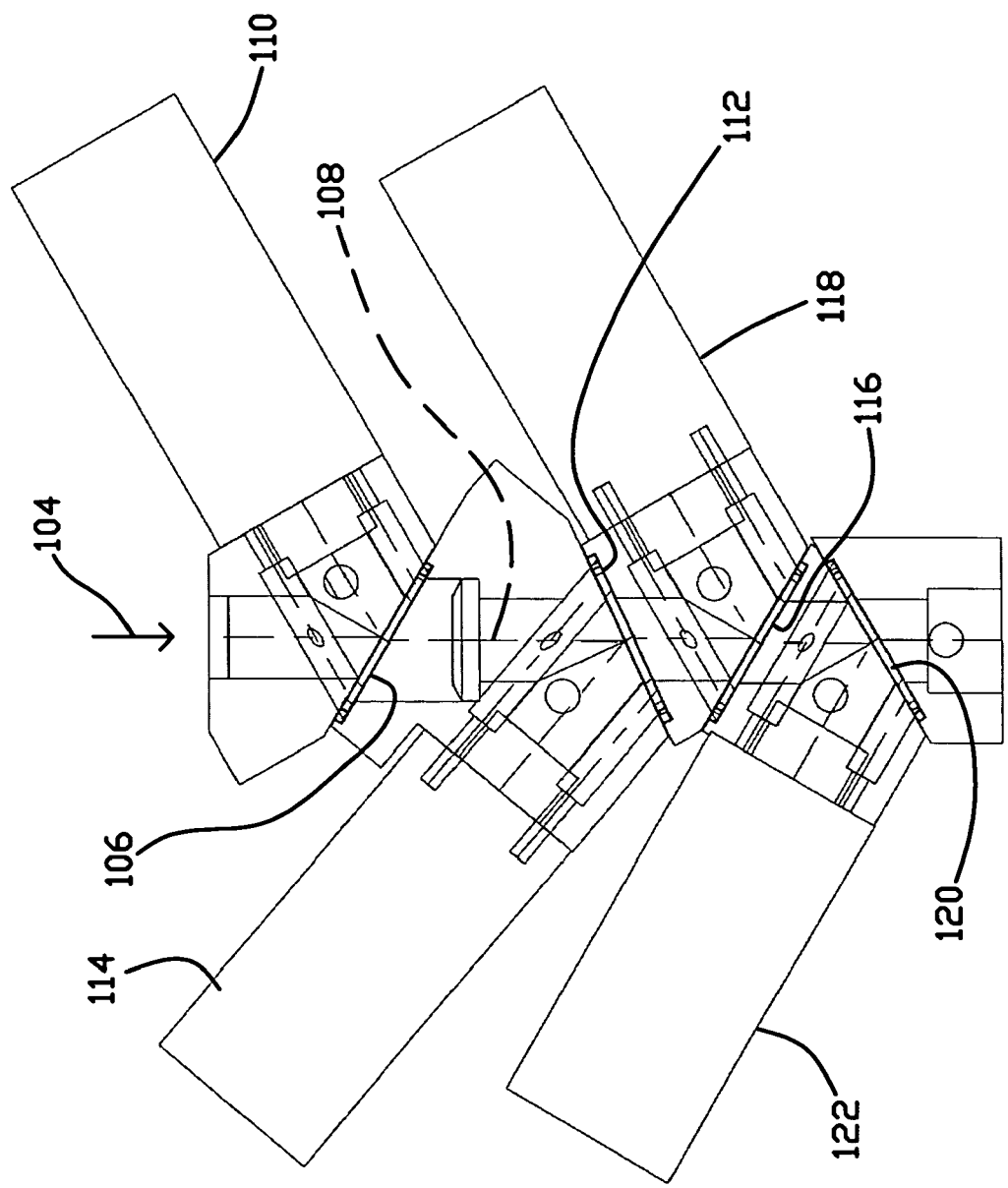
FIG. 4 is a side view of a portion of the prior art detector of FIG. 1.
Figure 5:
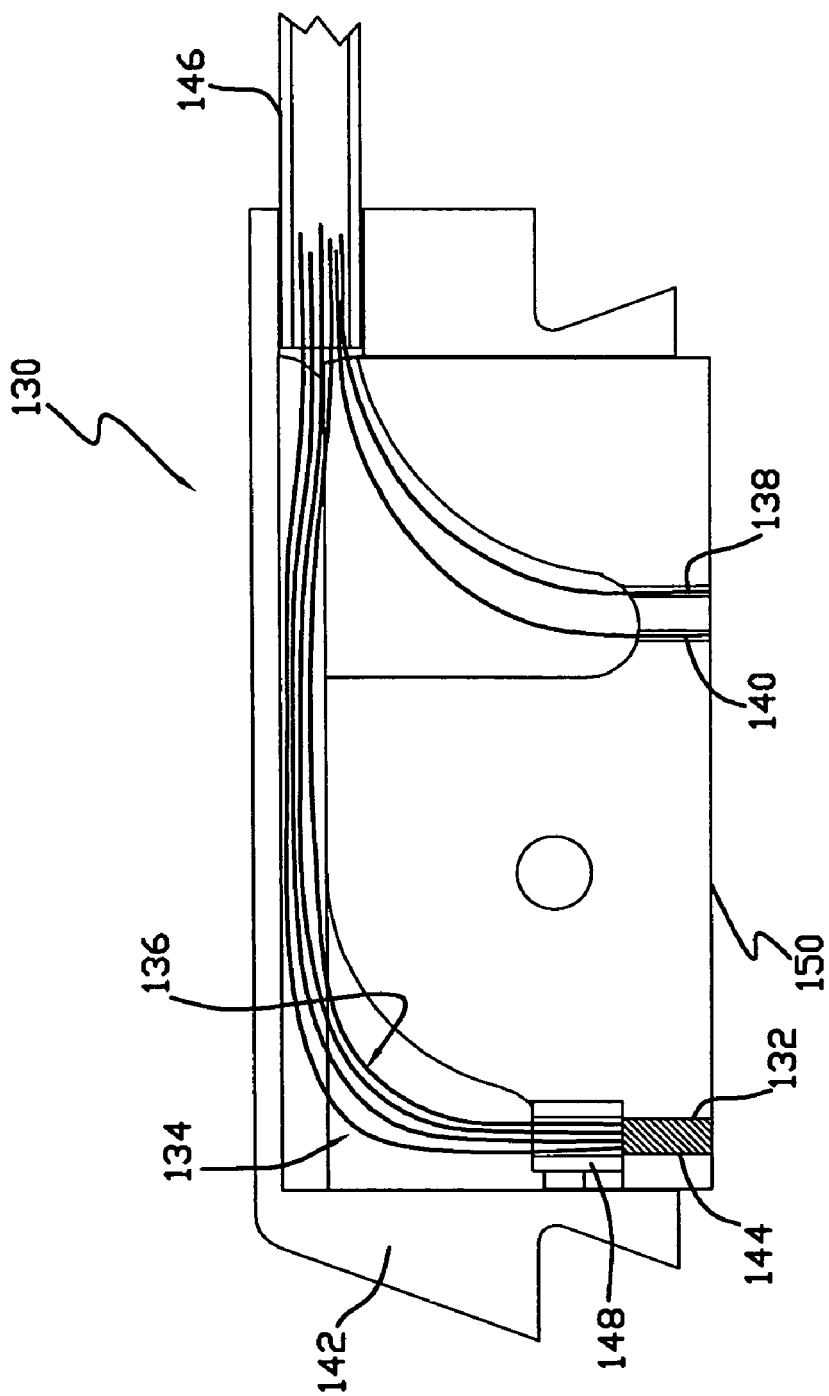
FIG. 5 is a side sectional view of a prior art probe.

Generally, the measurement light signals are significantly attenuated as they travel through the tissue sample. Thus, detectors for determining the strength of the collected light signals of the return optical path 224 or for converting the collected light signals to electrical signals (such as would be employed in the processor/controller 22 as shown in FIG. 1) need only accommodate a signal strength on the order of approximately 1% of the initial signal strength of the measurement light signals. The reference light signals, however, are not subject to tissue sample attenuation, and remain at approximately the same signal strength as the measurement light signals. Diffusing member 266 further serves to attenuate the signal strength of the reference light signals to approximately the same signal strength as the collected light signals. Doing so enables the same or similar detectors to be employed for both the reference light signals and the collected light signals. Comparison of the two is also facilitated because they are at about the same order of magnitude. According to one embodiment, diffuser 266 attenuates about 99% of the reference light signals. According to another embodiment, diffuser 266 attenuates the reference light signals to approximately the same signal strength as the measurement light signals collected by the return optical path 224.

According to various embodiments, diffusing member 266 may be a flashed opal diffuser of the type commonly used to diffuse light and available from optical component suppliers. Alternately, the diffusing member 266 may be a holographic or ground glass diffuser or a bulk scattering media.

Optical fibers, including send optical fibers 216, feedback optical fiber 268 and return optical fiber 218, are housed in the connector 208 extending between the electronics package 206 and the probe 202. In one embodiment, the probe 202 and connector 208 are a single integral and disposable unit. According to another embodiment, the distal end of the connector 208 is detachably coupleable to the probe housing 203. Optionally, the probe 202 and connector 208 are separate units coupled via a connector mechanism. According to one embodiment, the send, return and reference optical fibers 216, 218, 268 extend from the connector 208 through the aperture 205 and into the probe housing 203. According to another embodiment, any combination of the optical fibers interface with a coupling mechanism to transfer light signals from the connector 208 to the probe 202.

Connector 208 may be an electrical connector, an optical connector, a combination of the two or a wireless link such as an RF link, an IR link or other wireless communication scheme. The connector 208 is used to communicate between the probe 202 and the electronics package 206. In the case where a wireless connector is used, a power supply may be used with the probe 202 to provide power to the probe 202. The power supply may be a battery, fuel cell, capacitor, solar cell or the like.

Figure 7B:
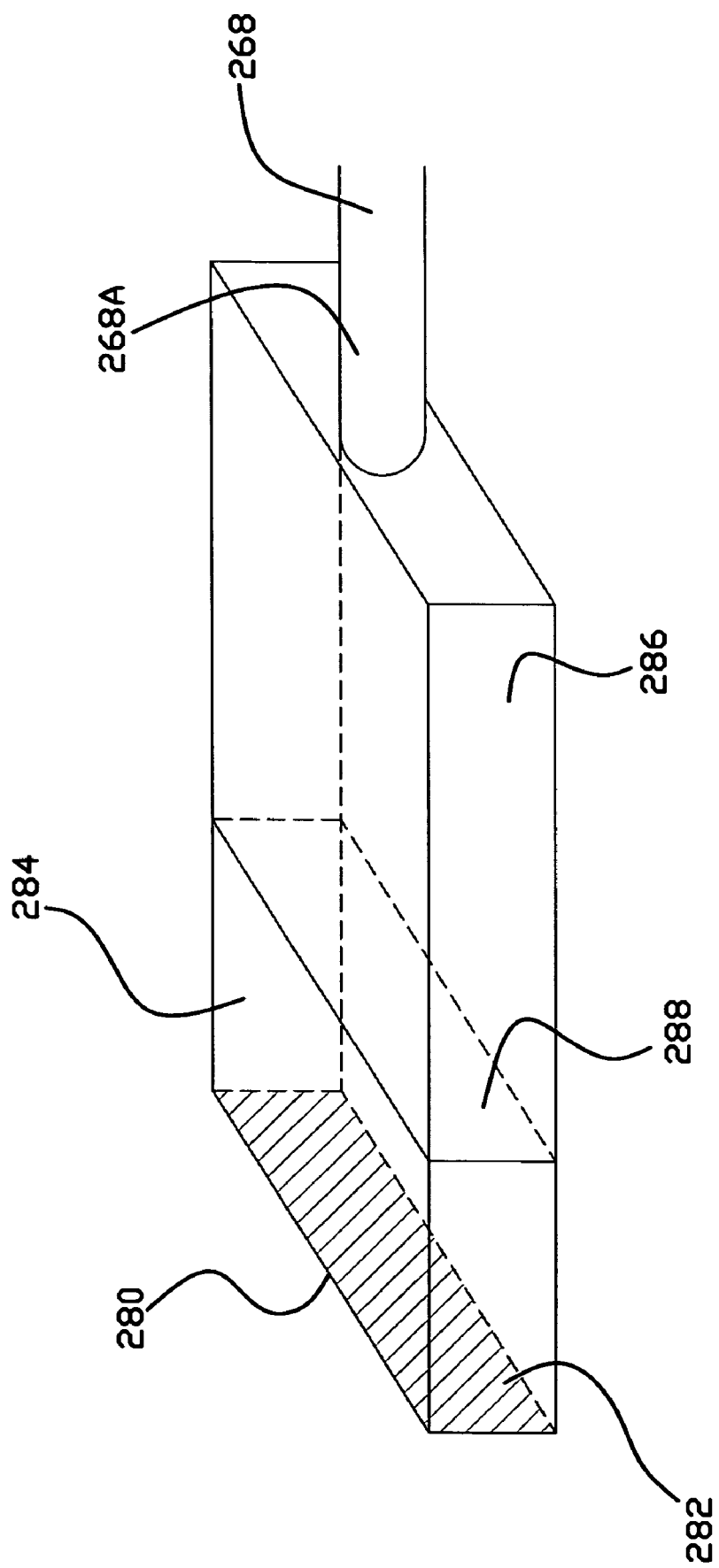
FIG. 7B is a perspective view of a portion of the reference optical path of FIG. 6 according to another embodiment of the present invention.

FIG. 7B shows a diffusing member 280 according to another embodiment of the present invention for use in place of diffusing member 266. Diffusing member 280 also serves to attenuate the strength of the reference light signals and to render the reference fiber coupling efficiency independent of reference light signal spatial and angular non-uniformity. The diffusing member 280 includes a surface scattering media 281 positioned on a first surface 282 of a glass block 284. An epoxy mass 286 extends from an opposite second surface 288 of the glass block 284 to the distal end 268*a* of the reference optical fiber 268. When the reflected reference light signals strike the surface scattering media 281, they are diffused into a generally spherical "cloud". The signal strength of the reference light signals is greater nearer the center of the "cloud" and becomes weaker, or is attenuated, towards the periphery of the "cloud". The epoxy mass 286 has a similar light transmitting index as the glass block 284. The epoxy mass 286 serves as a spacer between the "cloud" of diffused reference light signals at the surface scattering media 281 and the distal end 268*a* of the reference optical fiber 268. The size of the epoxy mass 286, and thus the spacing between the surface scattering media 281 and the distal end 268*a* of the reference optical fiber 281, is chosen such that the majority of the rays of reference light signals are received by the reference fiber 268 at an appropriate signal strength as described above.

Figure 8:
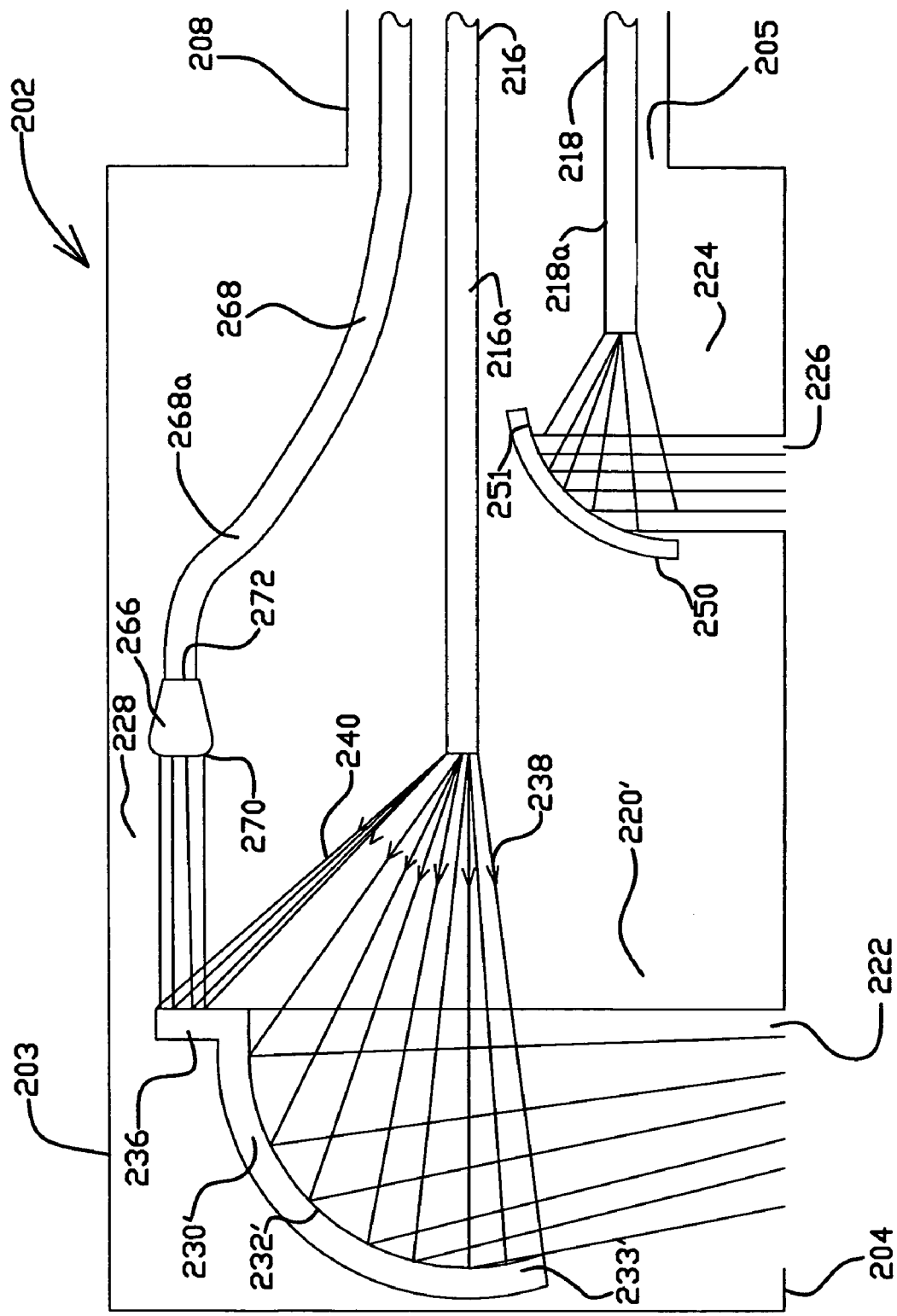
FIG. 8 is a side sectional view of the probe of FIG. 6 according to another embodiment of the present invention.

FIG. 8 shows the probe 202 according to another embodiment of the present invention. The reference optical path 228 and return optical path 224 are as described with respect to FIG. 7A. The delivery optical path 220, however, is altered as follows. A first portion 233' of the reflecting member 230' is formed with a curved shape such that reflective surface 232' of the first portion 233' has a generally elliptical profile. The reflecting member 230' is positioned such that the concave side faces the distal end 216*a* of the send optical fiber 216. As described previously, a portion of the beam of measurement light signals as shown by arrow 238 is directed at the reflective surface 232' of the first portion 233' and reflected onto the tissue sample through the delivery aperture 222. The curvature of the first portion 233' focuses or narrows the beam of measurement light signals reflected onto the tissue sample. The first portion 233' is shaped and positioned to capture substantially all or most of the light beams emanating outwardly from the send optical fiber 216.

Figure 9:
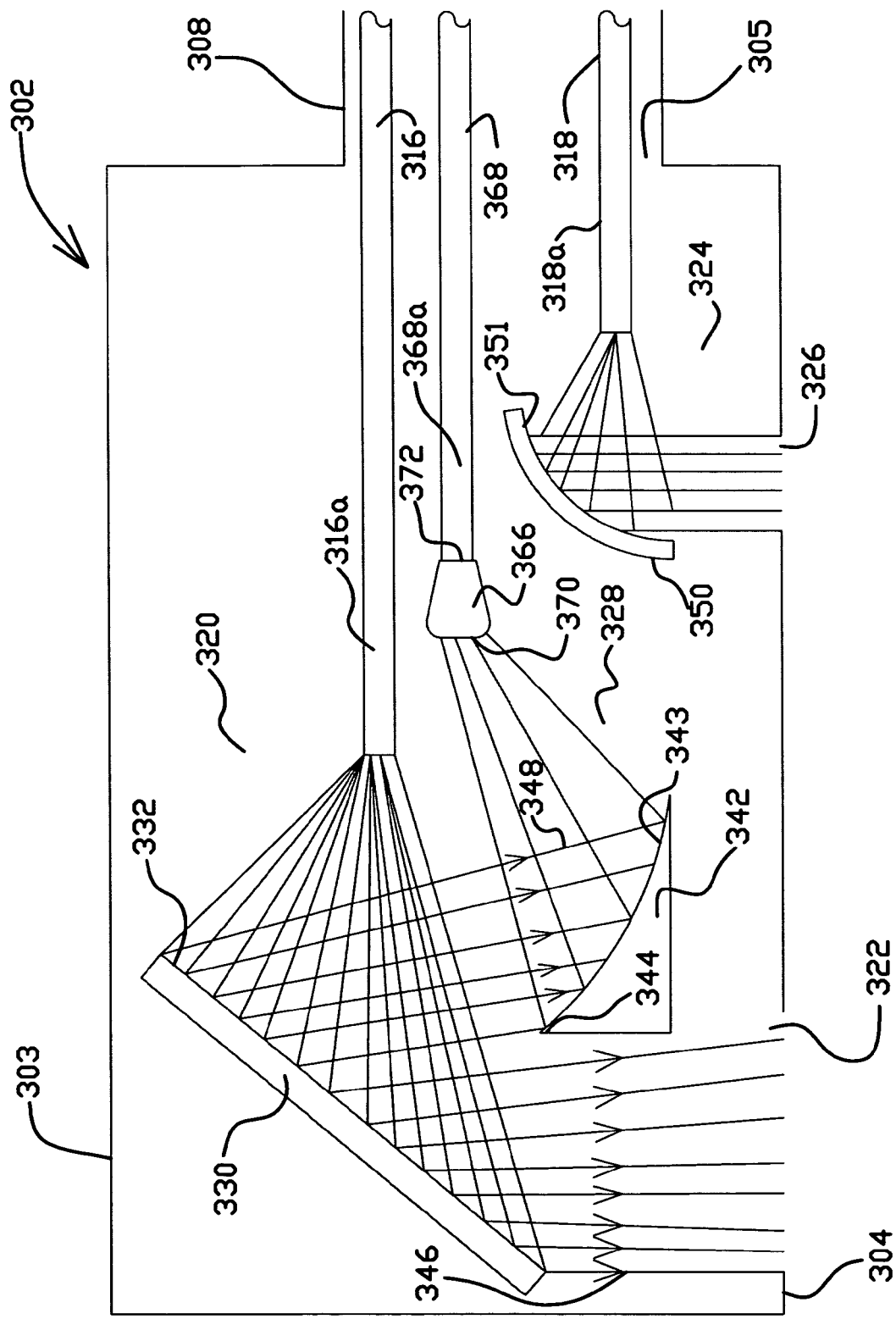
FIG. 9 is a side sectional view of the probe of FIG. 6 according to yet another embodiment of the present invention.

FIG. 9 illustrates a portion of a probe 302 according to another embodiment of the present invention. Probe 302 includes a probe housing 303 having a tissue engaging surface 304 coupled to a connector 308 such that send and return optical fibers 316, 318 extend into the housing 303 through an aperture 305 in the housing 303 as previously described. The probe 302 also includes a send optical path 320 coupled to the send optical fiber 316 and a return optical path 324 coupled to the reference optical fiber 318 as described with respect to FIG. 7A. The send optical path 320 further includes a first reflecting member 330 positioned adjacent the send optical fiber 316 for reflecting measurement light signals onto the tissue sample through an aperture 322 in the tissue engaging surface 304. The probe 302 further includes a reference optical path 328 for capturing a portion of the measurement light signals of the send optical path 320. The reference optical path 328 includes a second reflecting member 342 interposed between the first reflecting member 330 and the tissue engaging surface 304 of the probe housing 303.

The second or feedback reflecting member 342 has a reflective surface 343 and is positioned in the path of the measurement light signals after they have been reflected off of the first reflecting member 330 and prior to striking the tissue sample. Second reflecting member 342 is generally triangular or shaped like a pie-slice so as to have an apex 344. The second reflecting member 342 is also formed with a curved surface profile so that the concave reflective surface 343 faces a distal end 368*a* of the reference optical fiber 368.

Feedback reflecting member 342 is positioned within the housing 303 so that the apex 344 is approximately centered in the generally circular beam of measurement light signals directed toward the tissue sample from the first reflecting member 330. A first region of the beam of measurement light signals as represented by arrows 346 is reflected off of the reflective surface 332 of the first reflecting member 330 to the aperture 322 in the tissue engaging surface 304 and onto the tissue sample. A second region of the beam of measurement light signals as represented by arrows 348 is also reflected off of the reflective surface 330 but is intercepted by the second reflecting member 342. The measurement light signals of the second region 348 are reflected off of the second reflecting member 342 and diverted or directed to the reference optical path 328.

According to one embodiment, reflecting member 342 has an elliptical profile chosen to focus the reflected reference light signals onto the distal end 368*a* of the reference optical fiber 368. According to other embodiments, the reflecting member 342 has an elliptical profile chosen to focus the reflected reference light signals onto a diffusing member 366 coupled to the reference optical fiber 368. The reflecting member 342 is revolved to extend about an arc of approximately 36°. A reflective member 342 configured as such diverts approximately 10% of the measurement light signals overall. A greater or smaller ratio of light signals captured can be achieved by increasing or decreasing the angular extension of the reflecting member 342, i.e., the size of the pie-slice shape formed by the reflecting member 342 relative to the beam of measurement light signals. Optionally, the feedback reflecting member 342 is interposed between the distal end 316*a* of the send optical fibers 316 and the first reflecting member 330 to intercept measurement light signals before the measurement light signals are reflected off of the first reflecting member 330.

In some instances the measurement light signals are somewhat diffused and evenly spread out across the beam of signals, while in other instances the measurement light signals are concentrated in the center of the beam. Second reflecting member 342 diverts a pie-slice or wedge-shaped region 348 of the circular beam of measurement light signals. The pie-slice or wedge-shaped region 348 is an axis symmetric portion of the beam of measurement light signals. A feedback optical path 328 according to the present embodiment advantageously intercepts an axis symmetric sample of the measurement light beam whether the measurement light signals are concentrated in the center of the beam or radially dispersed. According to one embodiment, the first reflecting member 330 has a curved shape as described with respect to FIG. 8.

Figure 10:
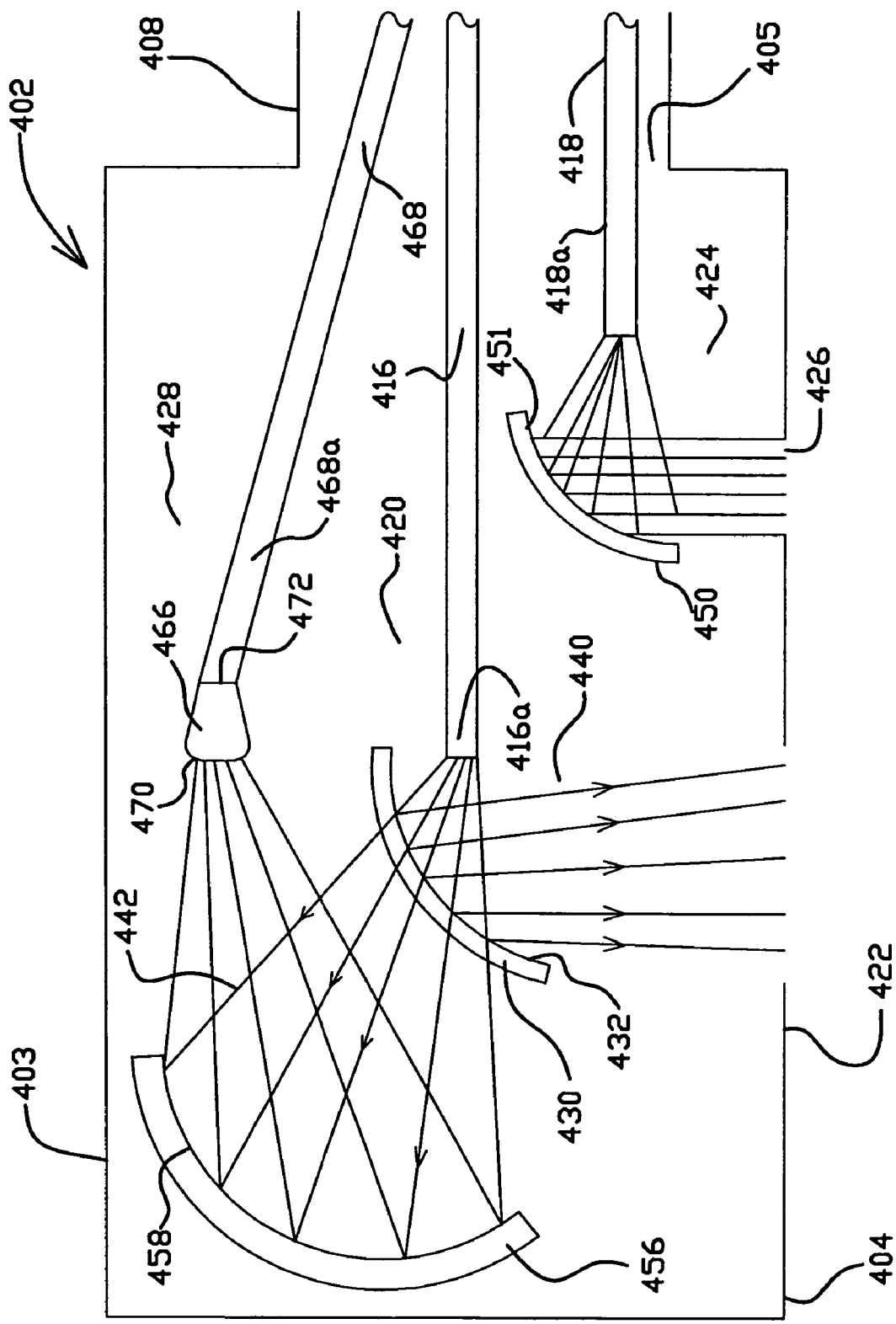
FIG. 10 is a side sectional view of the probe of FIG. 6 according to still another embodiment of the present invention.

FIG. 10 shows a probe 402 according to another embodiment of the present invention. Probe 402 includes a probe housing 403 having a tissue engaging surface 404 coupled to a connector 408 such that send and return optical fibers 416, 418 extend into the housing 403 through an aperture 405 in the housing 403 as previously described. The probe 402 includes a return optical path 424 coupled to the return optical fiber 418 as described with respect to FIG. 7A.

Probe 402 has a delivery optical path 420 including a first or delivery reflecting member 430 having a reflecting surface 432 positioned adjacent a distal end 416a of the send optical fiber 416. The reflecting member 430 is positioned relative to the distal end 416a of the send optical fiber 416 and the plane of the tissue engaging surface 404 to direct measurement light signals through a delivery aperture 422 in the tissue engaging surface 404 and onto the tissue sample. According to one embodiment, the reflecting member 430 is positioned at about a 45° angle with respect to distal end 416a of the send optical fiber 416 and the tissue engaging surface 404. The first reflective member 430 may be curved, as shown, or planar as described previously.

According to the present embodiment, the surface 432 of the first reflecting member 430 is only partially reflective. That is, a first portion of the measurement light signals as shown by arrow 440 are reflected as described above while a second portion of the measurement light signals as shown by arrow 442 are transmitted through the reflective surface 432, beyond the first reflective member 430 and into the reference optical path 428. A second reflective member 456 having a reflective surface 458 is positioned on the other side of the first reflective member 430. The second reflective member 456 is positioned to reflect the transmitted portion of the beam of measurement light signals off of the reflective surface 458 and onto a distal end 468a of a reference optical fiber 468. The second reflective member 456 may be curved, as shown, or may have a planar profile. The reference optical fiber 468 is shown coupled to a diffusing member 466 as previously described.

The partially reflective surface 432 of the first reflecting member 430 is formed of a coating of aluminum having a thickness of approximately 250 angstroms. According to other embodiments, the coating is a metallic material, for example gold or silver, or a multi-layer coating of a dielectric material. According to one embodiment, the partially reflective surface 432 has a reflection/transmission ratio of approximately 40:1. According to another embodiment, the reflection/transmission ratio of the partially reflective surface 432 is approximately 50:1. Generally, a higher reflection/transmission ratio is preferable. Further, it is generally preferable that the reflection/transmission ratio be consistent across the entire surface 432 and for all wavelengths regardless of the angle at which the reference light signals strike. According to one embodiment, the reflection/transmission ratio of the coating at a particular wavelength does not vary by more than approximately 1.125% across the surface 432 of the first reflective member 430. According to another embodiment, if the partially reflective coating is spectrally flat within approximately 0.25% (i.e., the reflection/transmission ratio is generally consistent for all wavelengths) then the reflection/transmission ratio may vary from one unit to the next between approximately 2–5%. According to yet another embodiment, if the partially reflective coating is not spectrally flat, then the reflection/transmission ratio bias from one unit to the next should be within approximately 1% and any variation across the surface 432 should be within approximately 0.25%.

Sometimes the measurement light signals are not evenly distributed about the center of the beam of measurement light signals. One cause of asymmetric distribution of the measurement light signals may be irregular bundling of the send optical fibers 416. Another source of asymmetric distribution may be caused by rotational misalignment between the send optical fibers 416 and the probe 402. However, a feedback optical path 428 according to the present embodiment samples the entire beam of measurement signals. The feedback optical path 428 provides a feedback sample representative of the entire beam of measurement light signals striking the tissue sample regardless of any asymmetry in wavelength distribution across the beam.

Figure 11:
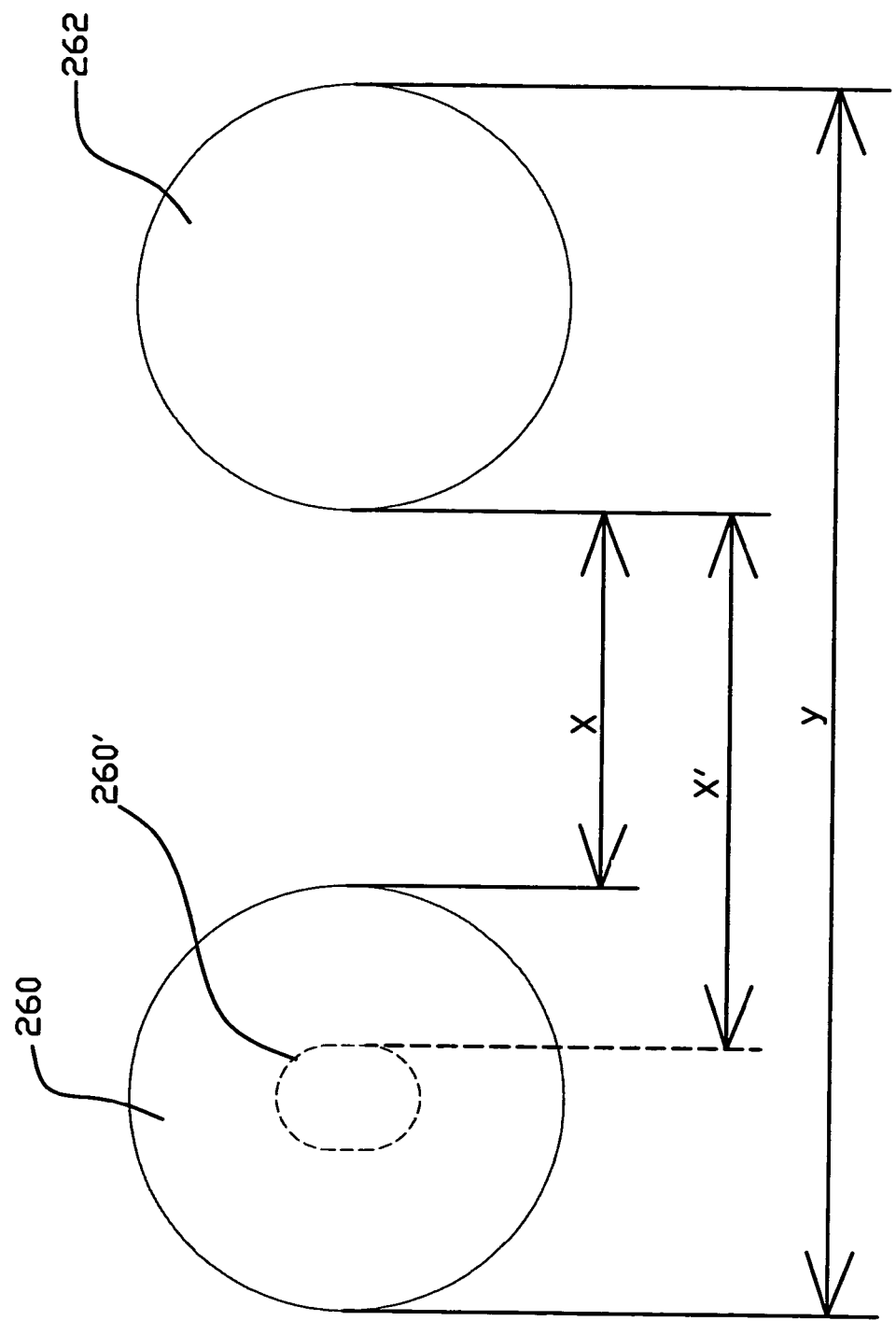
FIG. 11 is a top view detailing the pattern of measurement light signals striking and exiting a tissue sample according to the probes of FIGS. 7A–10.

Referring generally to FIG. 7A, FIG. 11 illustrates a pattern of the measurement light signals delivered to the tissue sample at the first aperture 220 and collected at the second aperture 228. The measurement light signals strike the tissue sample defining a delivery spot 260. Light signals, including measurement light signals, are in turn collected from an area on the tissue defining a reception region 262. The reception region 262 is spaced apart from the delivery spot 260 such that the measurement light signals travel a minimum distance X and a maximum distance Y between the delivery spot 260 and the reception region 262. The solid lines represent tissue sample patterns for probes such as those shown in FIGS. 7A and 9 in which the first reflective members 230, 330, respectively, are generally flat or planar. The broken lines represent the tissue sample pattern for probes 202 and 402 shown in FIGS. 8 and 10 in which the first reflective member 230', 430, respectively, has a curved or elliptical profile.

As described above, a reflective member having a curved or elliptical profile focuses or narrows the beam of measurement light signals reflected onto the tissue sample. Delivery spot 260' in turn has a reduced area such that the minimum linear traveling distance X' between the delivery spot 260' and the reception region 262 is increased. While the minimum linear traveling distance X has increased through the use of a delivery reflecting member having a curved profile, the distance between the apertures 222 and 226 may remain substantially the same. Further, the distance between components inside the probe 202, such as the distance between the delivery reflecting member 230 and the distal end 218a of the return optical fiber 218 remains substantially the same.

The linear distance the measurement light signals travel between the delivery spot 260 and the reception region 262 is indicative of the depth into the tissue sample the measurement light signals are transmitted. That is, measurement light signals collected from the tissue sample closer to the delivery spot 260 are transmitted through shallower layers of the tissue sample while measurement light signals collected from the tissue sample farther from the delivery spot 260 are transmitted through deeper layers of the tissue sample. In general, measurement light signals traveling less than approximately 11 mm between delivery spot 260 and reception region 262 are predominantly transmitted through shallow layers of skin and adipose tissue. Such a sampling distance sometimes produces an attenuated or inaccurate representation of tissue absorption because the transmitted light signals are representative of signal absorption by the skin and adipose layer, rather than signal absorption by the underlying tissue of interest. A probe according to the embodiments shown generally in FIGS. 8 and 10, therefore, provides an increased minimum sampling distance between the delivery spot 260' and the reception region 262 and improved quality of the collected light signals without requiring an increase in the size of the probe 202 to accommodate the increased sampling distance. The preferred minimum traveling distance varies according to the type of tissue being sampled. A probe according to the embodiment shown in FIG. 8 in which the reflecting member 230' has a curved or elliptical profile (see also FIG. 10) may be configured to provide a minimum traveling distance between the delivery of measurement light signals and the reception of light signals of from about 5 mm to about 35 mm.

Figure 12:
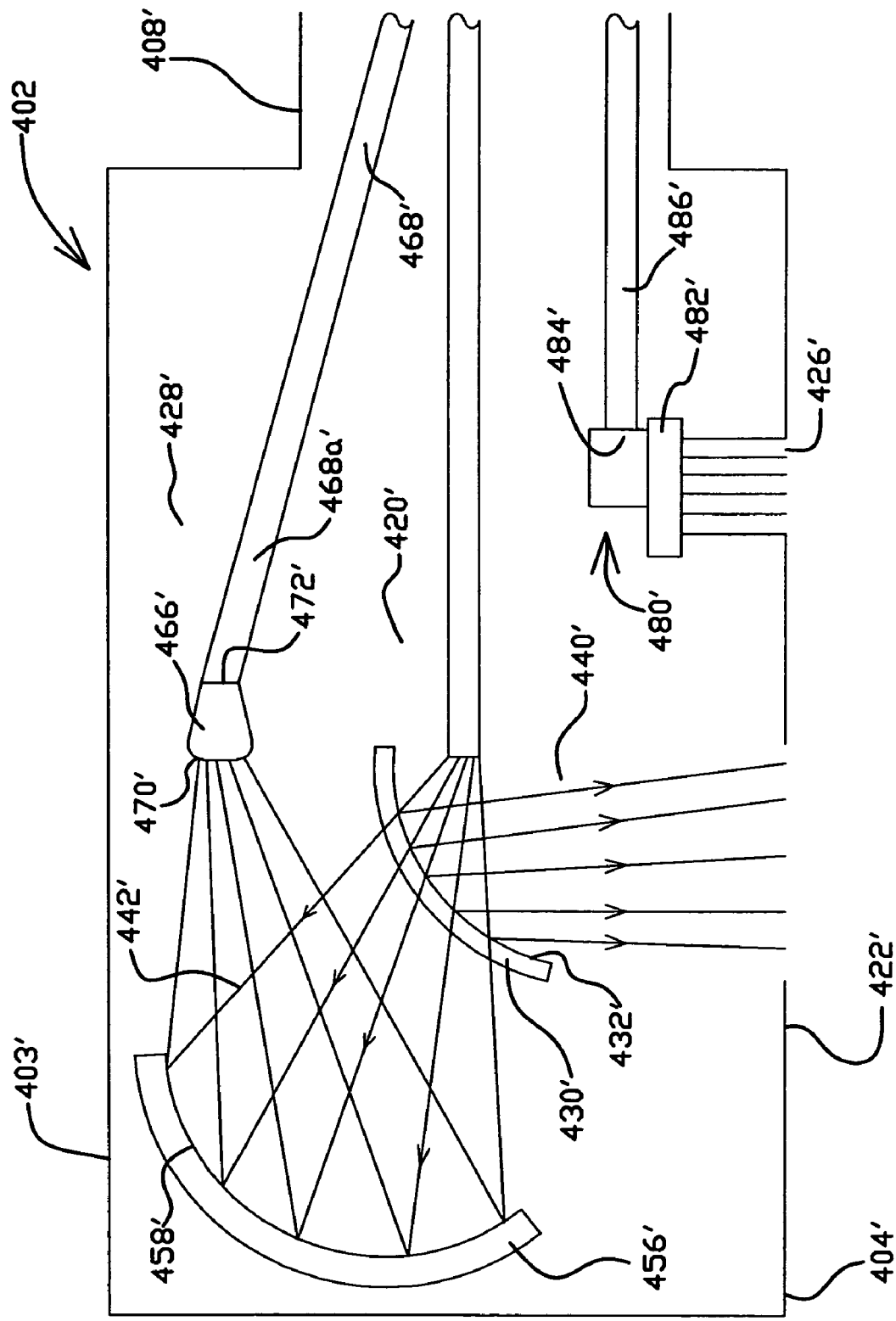
FIG. 12 is a side sectional view of the probe of FIG. 6 according to another embodiment of the present invention.

FIG. 12 shows a probe 402' according to another embodiment of the present invention. Probe 402' includes many of the features of probe 402 of FIG. 10, including a delivery optical path 420', a return optical path 424' and a reference optical path 428'. However, return optical path 424' includes a light detector, for example, a photodiode 480', for collecting light signals at the receive delivery aperture 426'. Photodiode 480' has an input 482' positioned to detect light signals from the tissue sample and an output 484' coupled to an electrical connector 486'. Photodiode 480' converts the input collected light signals into electrical signals for transmission along the electrical connector 486', which is in electrical communication with the electronics package 206 (See FIG. 6).

LEDs or other light sources sometimes exhibit drift or variation in both output measurement light signal wavelength or color and intensity. Such output signal instability may be up to 10% of signal, color and intensity. A drift of only 0.5% can sway the calculated saturated oxygen levels by 2 $StO_2$ units. Drift may be caused by both changes in ambient temperature and in component temperature as the LEDs warm up during operation of the spectrophotometric instrument. Measurement light signals are also subject to instability, including signal loss or drift as they travel from the measurement light signal source to the tissue sample. Drift in the measurement light signal may lead to inaccurate comparisons between the reference values associated with the light source wavelength and the collected light signals transmitted through the tissue sample.

A feedback compensation system according to the present invention provides a means for monitoring output signal instability, including drift in wavelength and intensity of the measurement light, by capturing a reference sample of the measurement light signal after it has traveled through substantially all of the delivery path. A reference sample of the measurement light signals is taken at the point where the measurement light signals are delivered to the tissue sample. The reference sample therefore includes all variations in wavelength or intensity of the measurement light signals throughout the delivery optical path up to the tissue sample. The reference sample is input to the processor/controller 210 as shown in FIG. 6. The processor 210 uses the reference sample to monitor output signal instability of the light source 214 and changes to the measurement light signals as they travel the delivery optical path 220. Such data may be used in a feedback mechanism to adjust the output of the light source 214 such that the frequency and intensity of the measurement light signals striking the tissue sample are within a desired range. Such data may also be used in an algorithm to provide a more accurate input value of the wavelength and intensity of the light striking the tissue sample when calculating the light absorption of the tissue sample.

According to typical prior art spectrophotometric instruments, a reference sample of the measurement light signals was typically taken at points on the delivery optical path of the measurement light signals significantly removed from the tissue sample, for example at the probe connector. A reference sample according to such an arrangement excludes all variations or drift in the measurement light signals along the delivery optical path between the probe connector and the tissue sample. A spectrophotometric instrument according to the present invention advantageously provides precise and accurate reference signals relating to the measurement light signals.

The feedback optical path further includes reference measurement light signals sampled from a sampling location in the path of the beam of measurement light signals striking the tissue sample. A sampling location placed to the side of the delivery aperture would tend to sample measurement light signals traveling at a greater angle of incidence than the light signals that strike the tissue through the delivery aperture. Such an arrangement would bias the reference sample in favor of those signals. Furthermore, a sampling location placed to the side of the aperture 216 would not correlate with the power actually being delivered to the tissue. The reference sample would show a peak power at a shorter wavelength than actually striking the tissue sample. In both cases, the reference sample would be biased, reducing the accuracy of compensation outcomes. A probe according to the present invention samples the beam of measurement light signals directed at the tissue sample at the delivery aperture, advantageously providing precise and accurate reference signals relating to the measurement light signals. Furthermore, the feedback optical path removes samples of the measurement light signals traveling the delivery optical path that are representative of the light signals striking the tissue. According to various embodiments as described previously, the feedback optical path samples or removes light signals from across the entire region of measurement light signals delivered to the tissue sample. A feedback compensation system according to the present invention uniformly samples the measurement light signals regardless of frequency or intensity. Furthermore, variations in the delivery optical path, i.e., irregularities in the positioning of the send optical fibers 216 as shown in FIG. 7A does not skew the representative sample.

Typical prior art instruments included calibration modules for frequently performing "blanking" procedures. For example, a "white" box was affixed to the probe and a calibration procedure was followed to re-set the reference values relating to the measurement light signals. A probe according to the present invention continuously provides feedback data based upon the feedback portion of the measurement light signals. It is unnecessary to frequently blank or reset the probe or to perform field calibrations to track wavelength drift. The calibration module or box of previous instruments is eliminated, reducing complexity of operation of the present instrument. Furthermore, operational data is immediately and continuously available.

Any of the above-described embodiments is a feedback means for sampling a portion of the measurement light signals representative of the measurement light signals striking the tissue sample. For example, the reflecting member 230 and portion 236 of FIG. 7A, the reflecting member 342 of FIG. 9, the partially transmissive reflecting member 430 and the second reflecting member 456 of FIG. 10 are all a feedback means for sampling a portion of the measurement light signals representative of the measurement light signals striking the tissue sample. A reference sample taken via any of the above described feedback means is then used for monitoring the output signal instability of the light source 214.

All of the aforementioned patents and publications are herein incorporated by reference. Although the present invention has been described in terms of particular embodiments, one of ordinary skill in the art, in light of this teaching, can generate additional embodiments and modifications without departing from the spirit of or exceeding the scope of the claimed invention. The foregoing description has been offered by way of example, not limitation. The applicant describes the scope of his invention through the claims appended hereto.

What is claimed is:

1. A probe for a spectrophotometric instrument, the probe comprising:
    a probe housing having a tissue engaging surface with first and second apertures extending therethrough;
    a first optical path having a proximal end optically coupleable to a light source and extending to a distal end optically coupled to the first aperture for delivering a beam of measurement light signals to a tissue sample;
    a first reflective member having a reflective surface and formed with a first portion positioned adjacent the distal end of the first optical path and the first aperture, wherein the reflective member reflects the measurement light onto the tissue sample;
    a second optical path having a distal end optically coupled to the first optical path adjacent the first aperture for sampling a reference light signal portion of the measurement light signals of the first optical path and extending to a proximal end coupleable to a processor; and
    a third optical path having a distal end optically coupled to the second aperture and extending to a proximal end coupleable to the processor.

2. The probe of claim 1 wherein the second optical path samples a discrete portion of the measurement light signals of the first optical path.

3. The probe of claim 1 wherein the second optical path samples an axis symmetric portion of the measurement light signals of the first optical path.

4. The probe of claim 1 wherein the second optical path samples from substantially the entire beam of the measurement light signals of the first optical path.

5. The probe of claim 1 wherein the first optical path further comprises:
    a first optical fiber having a proximal end provided with a light input region and extending to a distal end provided with a light output region, said distal end extending into the probe housing parallel to the tissue engaging surface and positioned adjacent the first aperture; and
    wherein the second optical path further includes a second optical fiber provided with a light input region at a distal end positioned within the probe housing and extending to a proximal end provided with a light output region.

6. The probe of claim 1, wherein the first portion of the first reflective member is positioned at an angle of about 45° relative to the tissue engaging surface.

7. The probe of claim 1, wherein the first portion of the first reflective member is positioned to reflect light onto the tissue sample substantially perpendicular to the plane of the surface tissue.

8. The probe of claim 1, wherein the first portion of the first reflective member has a concave curved profile.

9. The probe of claim 1, wherein the first portion has a planar profile.

10. The probe of claim 5, wherein the second optical path further comprises a second portion formed in the first reflective member at an angle relative to the first portion and wherein the distal end of the second optical fiber is positioned adjacent the second portion.

11. The probe of claim 5 wherein the second optical path further comprises a second reflective member having a reflective surface positioned between the first reflective member and the first aperture and wherein the distal end of the second optical fiber is positioned adjacent the second reflective member.

12. The probe of claim 1 wherein the reflective surface of the first reflective member is partially reflective and partially transmissive and the second optical path further comprises a second reflective member having a reflective surface positioned on the opposite side of the first reflective member as the first optical fiber and wherein the distal end of the second optical fiber is positioned adjacent the second reflective member.

13. The probe of claim 12 wherein the reflective surface of the first reflective member is comprised of one of aluminum, gold, silver or a dielectric.

14. The probe of claim 12 wherein the reflective surface of the first reflective member has a reflection/transmission ratio of approximately 40:1.

15. The probe of claim 12 wherein the reflective surface of the first reflective member has a reflection/transmission ratio of approximately 50:1.

16. The probe of claim 12 wherein the second reflective member has a concave curved profile.

17. The probe of claim 5 further comprising a light attenuator coupled to the distal end of the second optical fiber.

18. The probe of claim 17 wherein the attenuator is adapted to attenuate from about 97% to about 99% of the reference light signals.

19. The probe of claim 17 wherein the attenuator comprises a bulk scattering media.

20. The probe of claim 19 wherein the attenuator comprises:
    a first surface having a convex curved profile;
    a second surface optically coupled to the distal end of the second optical fiber; and
    a tapering region extending between the first surface and the second surface.

21. The probe of claim 17 wherein the attenuator comprises:
    a glass block;
    a surface scattering media formed on the glass block; and
    a light transmitting spacing member interposed between the glass block and the distal end of the second optical path.

22. The probe of claim 1 wherein the first aperture is spaced apart from the second aperture a minimum distance of from about 5 mm to about 35 mm.

23. The probe of claim 1 further comprising an optical connector coupled to the probe housing.

24. The probe of claim 23 wherein a distal end of the connector is detachably coupled to the probe housing.

25. The probe of claim 23 wherein a distal end of the connector is integrally formed with the probe housing.

26. The probe of claim 23 wherein a proximal end of the connector is optically coupleable to the light source and a distal end of the connector is optically coupled to the probe housing.

27. The probe of claim 23 wherein the connector further comprises at least one optical fiber.

28. The probe of claim 23 wherein a distal end of the connector is coupled to an interface mechanism coupled to the probe housing.

29. The probe of claim 1 wherein the light source emits light signals at about 800, 760, 720 and 680 nm.

30. The probe of claim 1 wherein the third optical path further comprises:
a reflective member having a reflective surface positioned adjacent the second aperture; and
an optical fiber having a distal end provided with a light input region positioned adjacent the reflective surface and a proximal end provided with a light output region.

31. The probe of claim 30 wherein the reflective surface has a concave curved profile.

32. A feedback system for monitoring output signal instability of a spectrophotometric instrument, the system comprising:
a probe having a tissue engaging surface with a first aperture extending therethrough;
a first optical path having a proximal end optically coupleable to a light source and extending to a distal end optically coupled to the first aperture for delivering a beam of measurement light signals to a tissue sample;
a first reflective member having a reflective surface and formed with a first portion positioned adjacent the distal end of the first optical path and the first aperture, wherein the reflective member reflects the measurement light onto the tissue sample; and
a second optical path having a distal end optically coupled to the first optical path adjacent the first aperture for sampling a portion of the measurement light signals of the first optical path and extending to a proximal end coupleable to a processor.

33. A probe for use with a spectrophotometric instrument, the probe comprising:
a probe housing having a tissue engaging surface with first and second apertures extending therethrough;
a first optical path having a proximal end optically coupleable to a light source and extending to a distal end optically coupled to the first aperture for delivering a beam of measurement light signals to a tissue sample;
a feedback means for removing a port ion of the measurement light signals from the first optical path adjacent the first aperture representative of the measurement light signals striking the tissue sample;
a third optical path having a distal end optically coupled to the second aperture and extending to a proximal end coupleable to a processor;
a first reflective member having a partially reflective surface positioned adjacent the first aperture for reflecting a portion of the measurement light signals of the first optical path through the first aperture and onto the tissue sample and for transmitting a portion of the measurement light signals; and
a second reflective member having a reflective surface positioned to reflect the measurement light signals transmitted through the first reflective member; and an optical fiber having a distal end adjacent the second reflective member for collecting light signals and extending to a proximal end coupleable to a processor.

34. The probe of claim 33 wherein the partially reflective surface has a reflection/transmission ratio of from about 40:1 to about 50:1.

35. The probe of claim 33 wherein the partially reflective surface has a substantially wavelength neutral reflection/transmission ratio.

36. A method for monitoring output signal instability in a spectrophotometric instrument, the method comprising:
providing a probe having a tissue engaging surface for delivering measurement light signals to a tissue sample and for receiving light emitted from the tissue sample;
providing a light source assembly for generating the measurement light signals, said light source assembly comprising:
a light source; and
at least one send optical fiber optically coupling the light source to the probe, said send optical fiber having a proximal end optically coupled to the light source and extending to a distal end protruding into the probe parallel to the tissue engaging surface;
delivering measurement light signals from the light source assembly to the probe through the send optical fiber;
reflecting the measurement light signals from the distal end of the send optical fiber onto the tissue sample; and
removing a reference sample of the measurement light signals representative of the measurement light signals reflected onto the tissue sample.

37. The method of claim 36 further comprising removing the reference sample from the measurement light signals adjacent the tissue engaging surface of the probe.

38. The method of claim 36 further comprising:
providing a first reflecting member having a partially reflective/partially transmissive surface adjacent the distal end of the send optical fiber for reflecting a first portion of the measurement light signals onto the tissue sample and transmitting a second portion of the measurement light signals through to the opposite side of the first reflecting member; and
providing a second reflecting member to reflect the second portion of the measurement light signals away from the tissue sample to form the reference sample.

39. The method of claim 36 flirt her comprising attenuating the reference sample to an intensity level approximately equal to an intensity level of the light emitted from the tissue sample.

* * * * *

UNITED STATES PATENT AND TRADEMARK OFFICE
CERTIFICATE OF CORRECTION

| | | |
|---|---|---|
| PATENT NO. | : 7,239,385 B2 | Page 1 of 1 |
| APPLICATION NO. | : 10/999260 | |
| DATED | : July 3, 2007 | |
| INVENTOR(S) | : Roger W. Schmitz et al. | |

It is certified that error appears in the above-identified patent and that said Letters Patent is hereby corrected as shown below:

Col. 19, line 37, delete "port ion" and insert --portion--.
Col. 20, line 46, delete "flirt her" and insert --further--.

Signed and Sealed this

Twenty-first Day of August, 2007

JON W. DUDAS
*Director of the United States Patent and Trademark Office*